US012537113B2

(12) United States Patent
Kondo et al.

(10) Patent No.: US 12,537,113 B2
(45) Date of Patent: Jan. 27, 2026

(54) CARBON ION GENERATING DEVICE

(71) Applicant: National Institutes for Quantum Science and Technology, Chiba (JP)

(72) Inventors: Kotaro Kondo, Chiba (JP); Sadaoki Kojima, Chiba (JP); Hiromitsu Kiriyama, Chiba (JP); Mamiko Nishiuchi, Chiba (JP); Hironao Sakaki, Chiba (JP); Masaki Hashida, Kyoto (JP); Syunsuke Inoue, Kyoto (JP)

(73) Assignee: National Institutes for Quantum Science and Technology, Chiba (JP)

( * ) Notice: Subject to any disclaimer, the term of this patent is extended or adjusted under 35 U.S.C. 154(b) by 413 days.

(21) Appl. No.: 18/245,703

(22) PCT Filed: Oct. 29, 2021

(86) PCT No.: PCT/JP2021/040050
§ 371 (c)(1),
(2) Date: Mar. 16, 2023

(87) PCT Pub. No.: WO2022/092271
PCT Pub. Date: May 5, 2022

(65) Prior Publication Data

US 2023/0360819 A1 Nov. 9, 2023

(30) Foreign Application Priority Data

Oct. 30, 2020 (JP) ................................ 2020-183098

(51) Int. Cl.
*G21K 5/04* (2006.01)
*A61N 5/10* (2006.01)
(Continued)

(52) U.S. Cl.
CPC ................ *G21K 5/04* (2013.01); *A61N 5/10* (2013.01); *G21K 1/00* (2013.01); *H01J 27/24* (2013.01); *A61N 2005/1088* (2013.01)

(58) Field of Classification Search
CPC ... G21K 5/04; G21K 1/00; A61N 5/10; A61N 2005/1088; A61N 5/1077; H01J 27/24
See application file for complete search history.

(56) References Cited

U.S. PATENT DOCUMENTS

2004/0016641 A1* 1/2004 Kolpakov ................ G21K 5/04
118/723 VE
2008/0290297 A1 11/2008 Blasche et al.
(Continued)

FOREIGN PATENT DOCUMENTS

CN 101023715 A 8/2007
CN 103313502 A 9/2013
(Continued)

OTHER PUBLICATIONS

Torrisi, et al., "Ion acceleration by fs laser in target-normal-sheath-acceleration regime and comparison of time-of-flight spectra with particle-in-cell simulations", Physical Review Accelerators and Beam, American Physical Society, Jan. 15, 2020, pp. 011034-1-011-039, vol. 23.
(Continued)

*Primary Examiner* — David A Vanore
(74) *Attorney, Agent, or Firm* — NK Patent Law

(57) ABSTRACT

Generation of impurity ions is prevented or reduced in a carbon ion generating device in which a laser-driven ion acceleration system is employed. A carbon ion generating device generates a carbonized region by irradiating a film made of an organic compound with a first laser beam, and generates carbon ions by irradiating at least a part of the carbonized region with a second laser beam.

14 Claims, 10 Drawing Sheets

Figure 1:
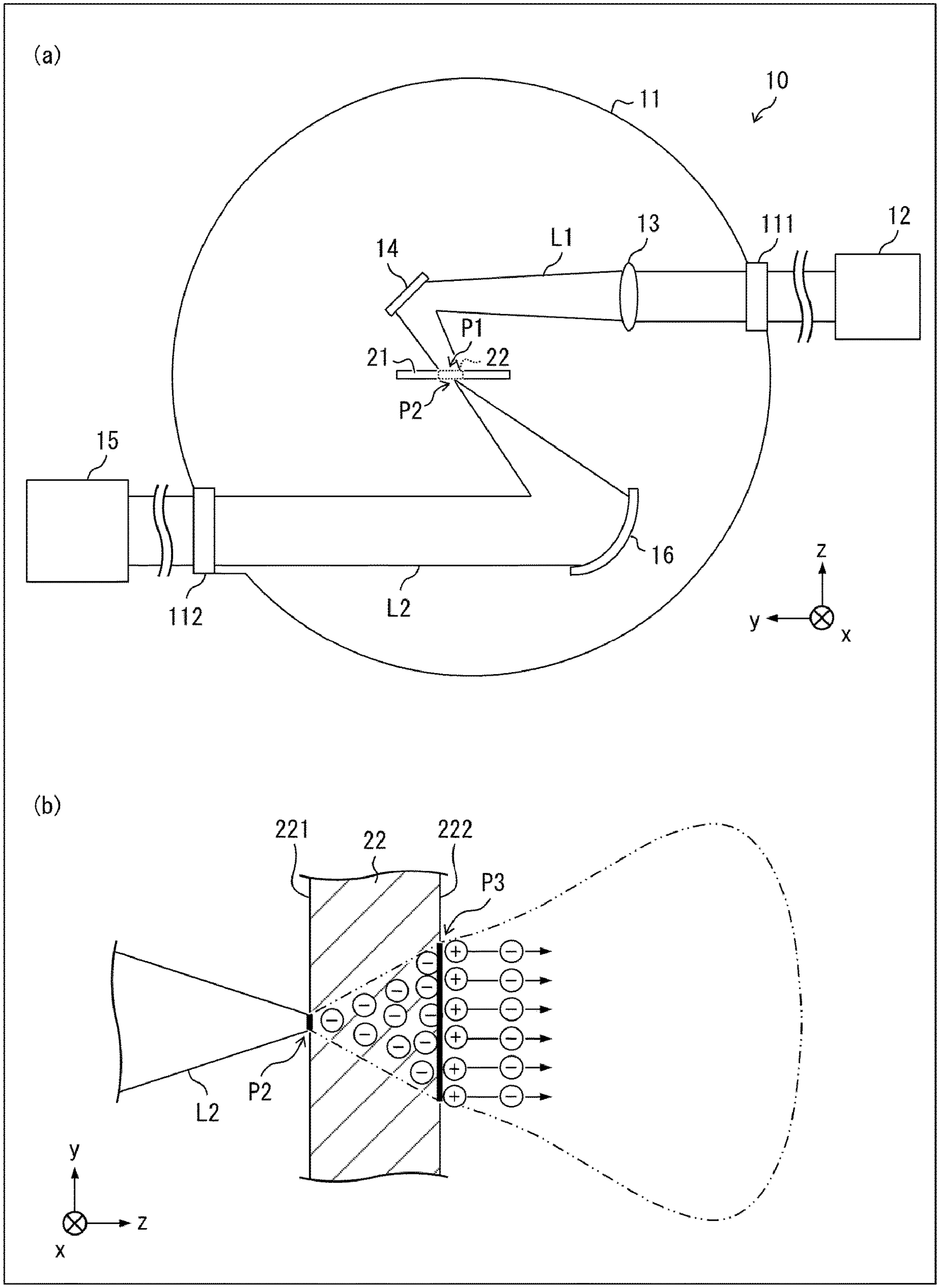

(51) Int. Cl.
*G21K 1/00* (2006.01)
*H01J 27/24* (2006.01)

(56) References Cited

U.S. PATENT DOCUMENTS

| | | | | |
|---|---|---|---|---|
| 2011/0096385 | A1* | 4/2011 | Suzuki | H05H 15/00 359/227 |
| 2011/0101237 | A1* | 5/2011 | Jung | H01J 37/08 977/950 |
| 2011/0273115 | A1* | 11/2011 | Liu | H05H 15/00 315/500 |
| 2013/0138184 | A1* | 5/2013 | Jung | H01J 27/02 427/122 |
| 2013/0234036 | A1 | 9/2013 | Kakutani et al. | |
| 2013/0261369 | A1* | 10/2013 | Jung | H01J 37/08 600/1 |
| 2013/0289331 | A1* | 10/2013 | Jung | H01J 27/02 600/1 |
| 2014/0135562 | A1* | 5/2014 | Jung | H01J 27/24 600/1 |
| 2015/0123009 | A1* | 5/2015 | Shin | H01J 27/24 250/423 P |
| 2015/0272677 | A1* | 10/2015 | Jung | A61B 18/22 606/16 |
| 2016/0317837 | A1* | 11/2016 | Benlloch Baviera | H01J 27/24 |
| 2017/0128739 | A1* | 5/2017 | Dilmanian | A61N 5/1084 |

FOREIGN PATENT DOCUMENTS

| | | | |
|---|---|---|---|
| CN | 210186258 | U | 3/2020 |
| JP | 2008-022994 | A | 2/2008 |
| JP | 2011-108641 | A | 6/2011 |
| JP | 2012-142248 | A | 7/2012 |
| WO | 2018112261 | A1 | 6/2018 |

OTHER PUBLICATIONS

KOTARO KONDO et al., "Laser-driven ion acceleration experiment using heated polyimide tape targets", Proceedings for 75th Annual Meeting, The Physical Society of Japan, Web version: ISSN 2189-0803, DVD version: ISSN 2189-079X, Mar. 16-19, 2020 Nagoya University 559, pp. 1-3.
ISA/JP, International Preliminary Report on Patentability for corresponding PCT Patent Application No. PCT/JP2021/040050, mailed May 2, 2023, 7 pages.
ISA/JP, International Search Report for corresponding PCT Patent Application No. PCT/JP2021/040050, mailed Jan. 18, 2022, 4 pages.
CNIPA; The First Office Action issued in corresponding Chinese Patent Application No. 202180063550.6, dated Jul. 16, 2025, 13 pages.

* cited by examiner

Irradiation interval: 0 sec

Irradiation interval: 1 sec

Irradiation interval: 5 sec

Irradiation interval: 15 sec

Irradiation interval: 60 sec

CARBON ION GENERATING DEVICE

CROSS-REFERENCE TO RELATED APPLICATIONS

This application is a U.S. National Stage Application of International Patent Application No. PCT/JP2021/040050, filed on Oct. 29, 2021, which claims priority to Japanese Patent Application No. 2020-183098, filed on Oct. 30, 2020, the entire contents of all of which are incorporated by reference herein.

TECHNICAL FIELD

The present invention relates to a carbon ion generating device.

BACKGROUND ART

In heavy ion cancer therapy, a linear accelerator and a synchrotron are used to accelerate, to predetermined energy, carbon ions generated in a carbon ion generating device, and then irradiate a tumor with the accelerated carbon ions.

Non-patent Literature 1 discloses a carbon ion generating device that generates carbon ions by irradiating a film made of carbon with a high-power laser beam. Such a system is called a laser-driven ion acceleration system. In a case where one (hereinafter referred to as a "front surface") of surfaces of the film is irradiated with a high-power laser beam, a large number of high energy electrons are ejected from the other (hereinafter referred to as a "back surface") of the surfaces of the film. This results in generation of an intense sheath electric field of the order of TV/m on or near the back surface, so that carbon ions are accelerated from the film by the sheath electric field. Thus, the carbon ion generating device in which the laser-driven ion acceleration system is employed makes it possible to generate carbon ions in an accelerated state.

CITATION LIST

Non-Patent Literature

[Non-patent Literature 1]
L. Torrisi et. al., Physical Review Accelerators Beams., 23, 011304 (2020).

SUMMARY OF INVENTION

Technical Problem

However, a conventional carbon ion generating device in which the laser-driven ion acceleration system is employed has a problem of generation of not only carbon ions but also impurity ions (e.g., oxygen ions) other than the carbon ions. This is because on a film surface, impurities such as water are adsorbed, and an impurity layer is formed.

An aspect of the present invention has been made in view of the problem described earlier, and an object thereof is to prevent or reduce generation of impurity ions in a carbon ion generating device in which a laser-driven ion acceleration system is employed.

Solution to Problem

In order to attain the object, a carbon ion generating device in accordance with an aspect of the present invention includes: a first laser irradiation mechanism that generates a carbonized region by irradiating a part of a film made of an organic compound with a first laser beam so as to carbonize the part; and a second laser irradiation mechanism that generates carbon ions from the carbonized region by irradiating at least a part of the carbonized region with a second laser beam.

Advantageous Effects of Invention

An aspect of the present invention makes it possible to prevent or reduce generation of impurity ions in a carbon ion generating device in which a laser-driven ion acceleration system is employed.

BRIEF DESCRIPTION OF DRAWINGS (a) of FIG. 1 is a view schematically illustrating a carbon ion generating device in accordance with Embodiment 1 of the present invention. (b) of FIG. 1 is a cross-sectional view obtained by enlarging a carbonized region of a film that is used in the carbon ion generating device illustrated in (a) of FIG. 1.

Figure 2:
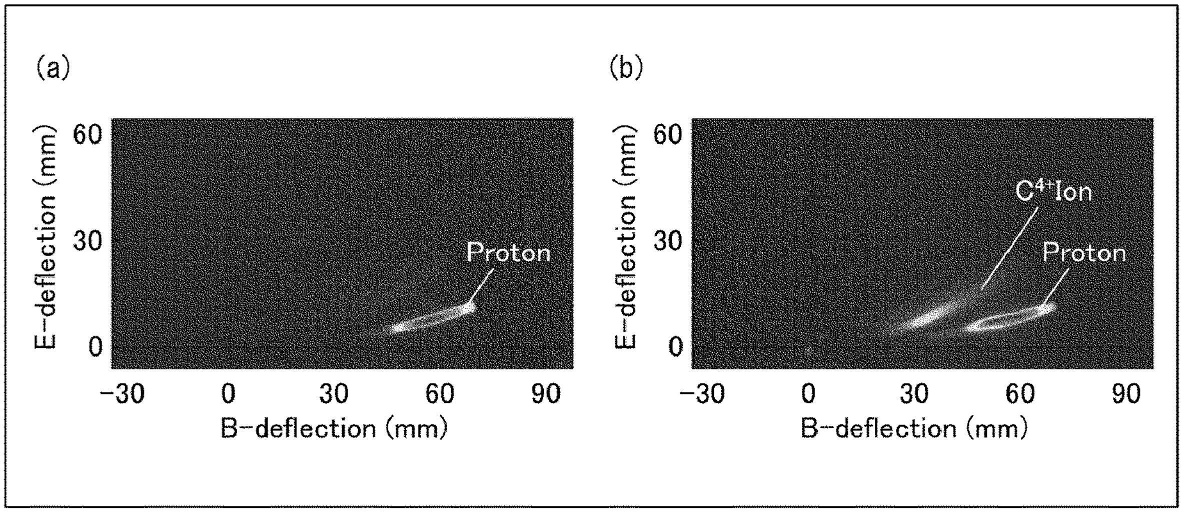

(a) and (b) of FIG. 2 are images showing energy distributions of ions generated with use of Comparative Example 1 and Example 1 of the present invention.

Figure 3:
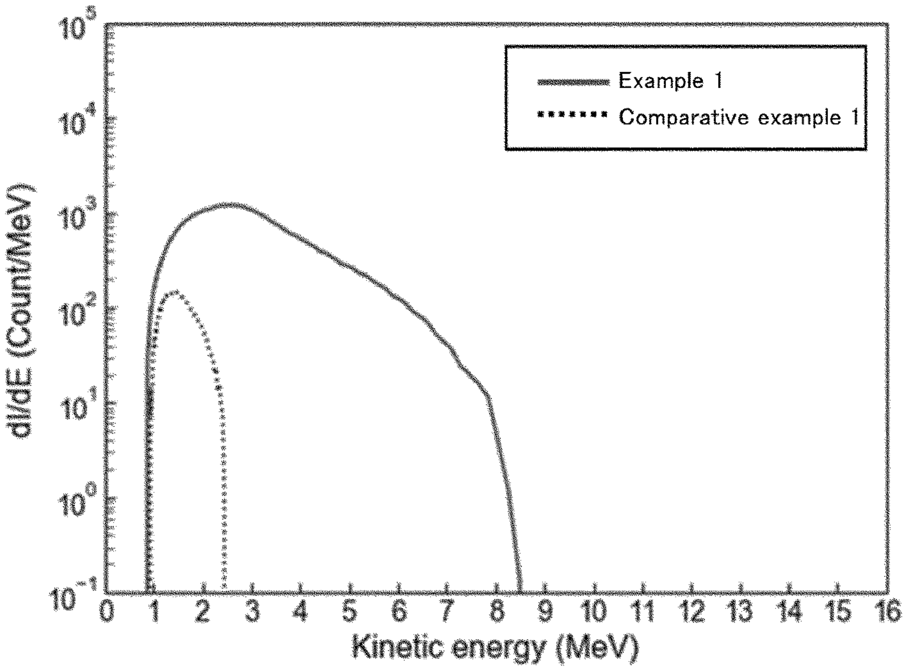

FIG. 3 is a graph showing energy spectra of carbon ions generated with use of Comparative Example 1 and Example 1 of the present invention.

Figure 4:
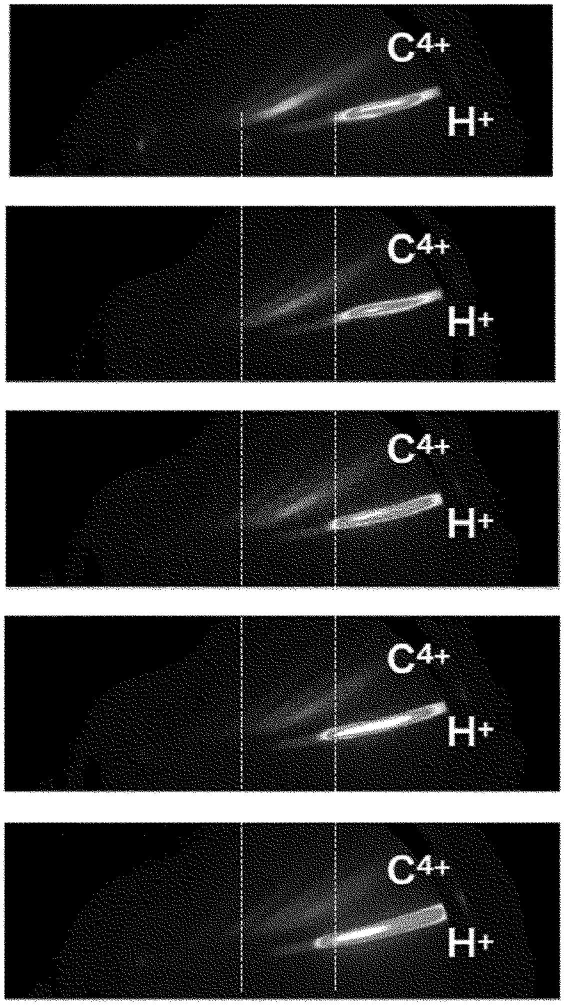

FIG. 4 has images showing energy distributions of ions generated by Example 1 of the present invention and by a case where an irradiation interval between irradiation with a first laser beam and irradiation with a second laser beam was changed to 1 second, 5 seconds, 15 seconds, and 60 seconds in Group of Examples 2 of the present invention.

Figure 5:
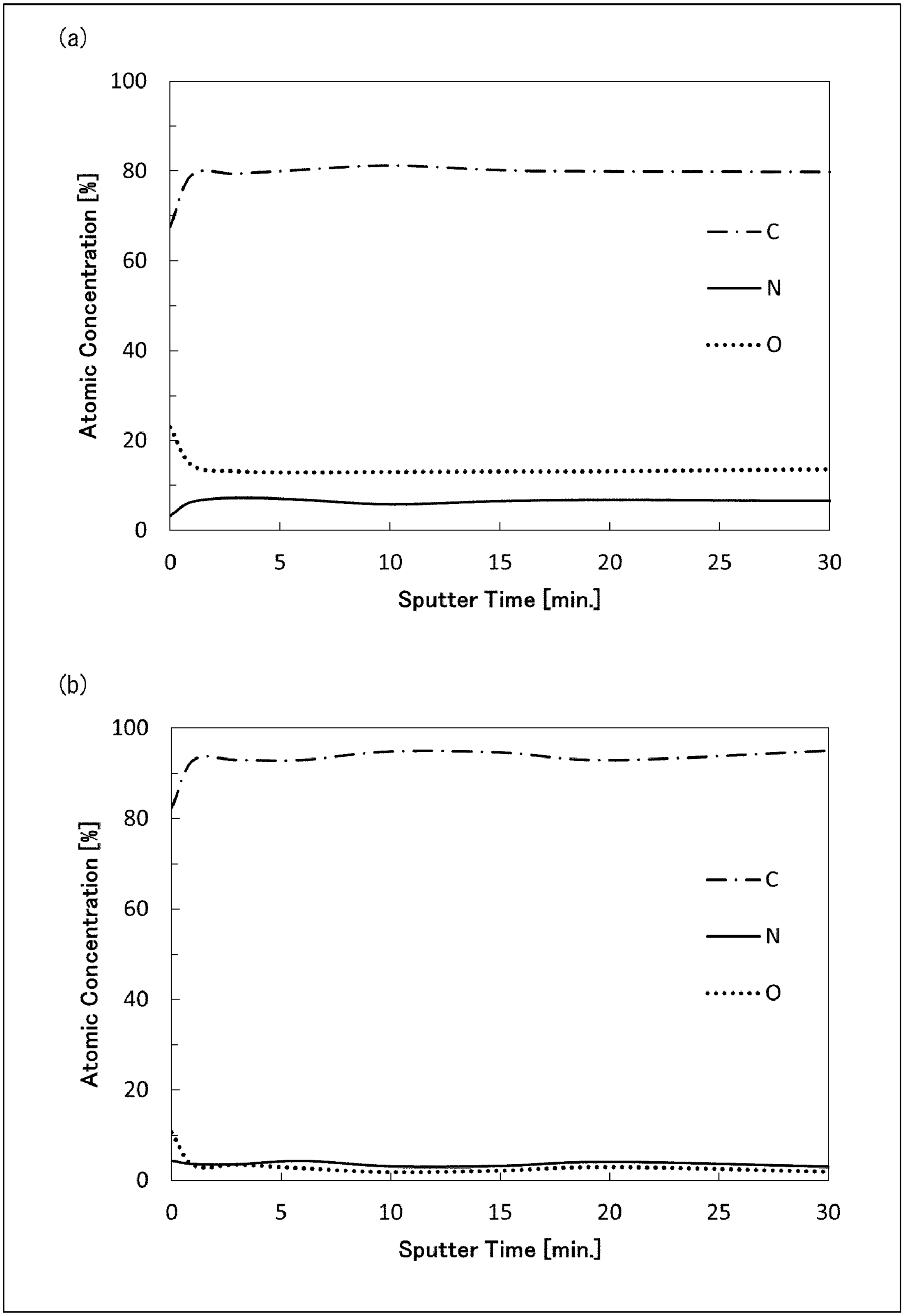

(a) and (b) of FIG. 5 are graphs showing depth dependence of composition ratios of films used in Comparative Example 2 and Example 3 of the present invention.

Figure 6:
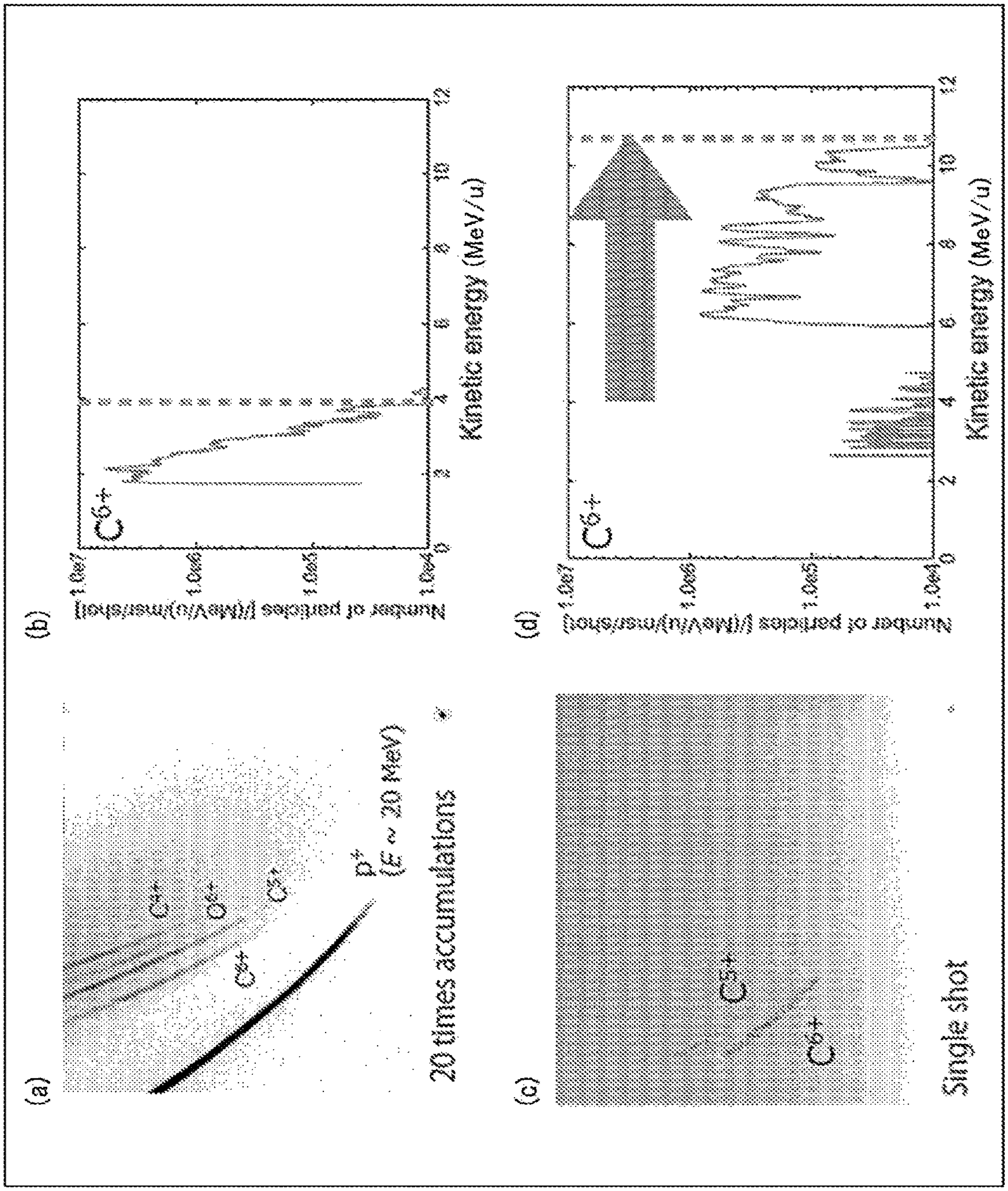

(a) and (c) of FIG. 6 are images showing energy distributions of ions generated with use of Comparative Example 2 and Example 3. (b) and (d) of FIG. 6 are graphs showing energy spectra of ions generated with use of Comparative Example 2 and Example 3.

Figure 7:
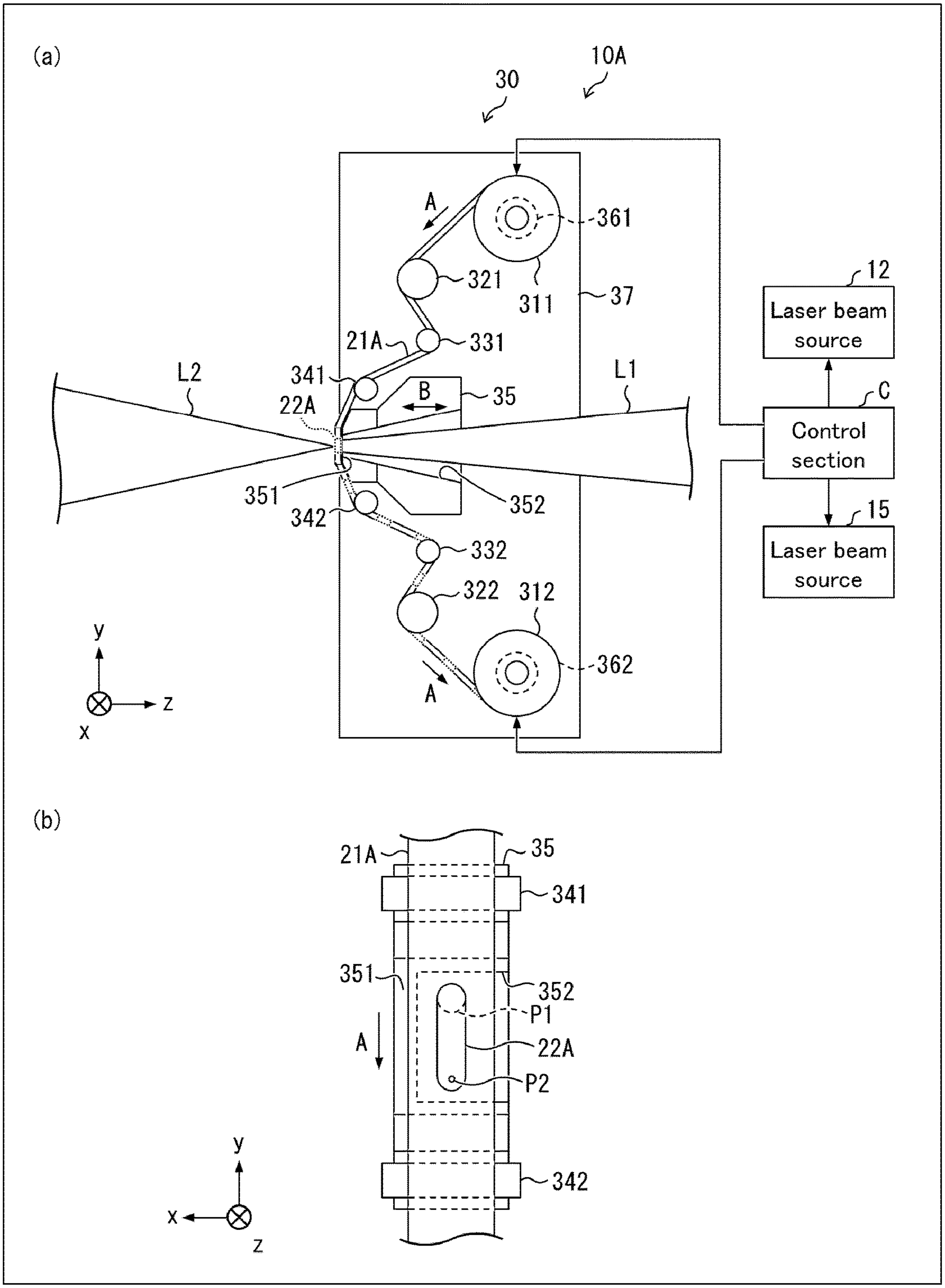

(a) of FIG. 7 is a side view of a continuous film-feed device of a carbon ion generating device in accordance with Embodiment 2 of the present invention. (b) of FIG. 7 is a plan view of a head surface of a variation of a tape head illustrated in (a) of FIG. 7.

Figure 8:
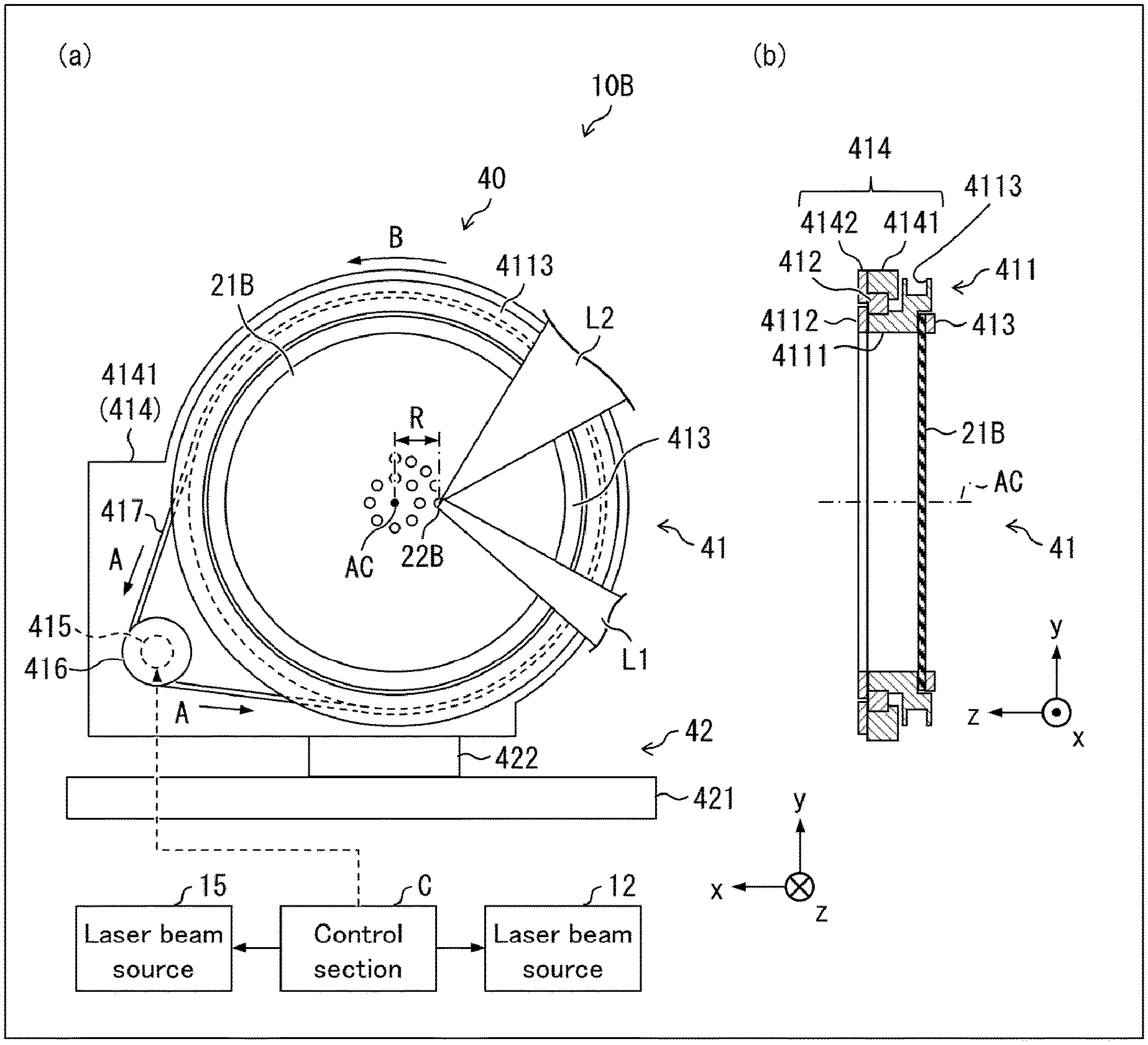

(a) of FIG. 8 is a plan view of a continuous film-feed device of a carbon ion generating device in accordance with Embodiment 3 of the present invention. (b) of FIG. 8 is a cross-sectional view of a rotational movement stage of the continuous film-feed device illustrated in (a) of FIG. 8.

Figure 9:
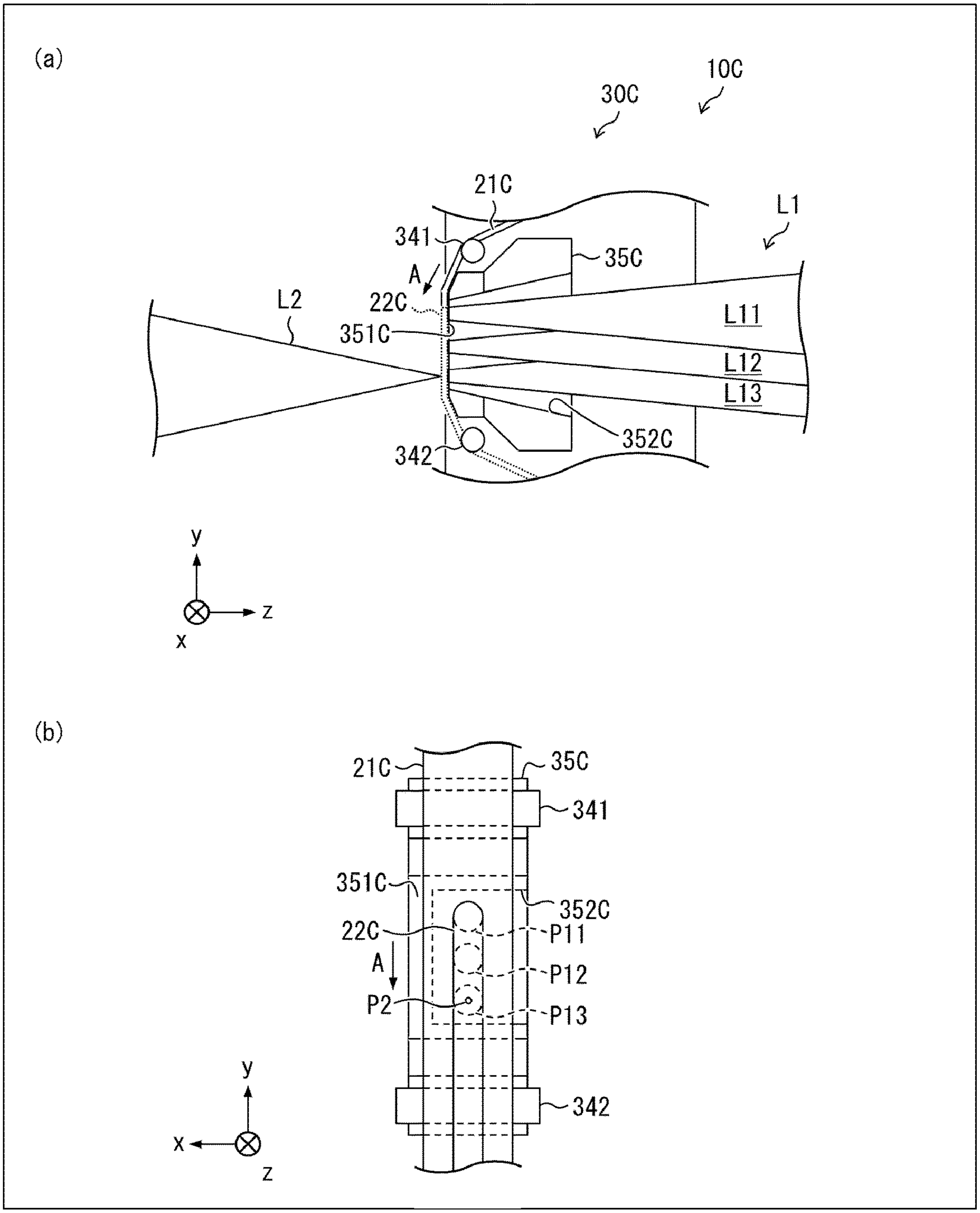

(a) of FIG. 9 is a side view of a continuous film-feed device of a carbon ion generating device in accordance with Embodiment 4 of the present invention. (b) of FIG. 9 is a plan view of a head surface of a tape head illustrated in (a) of FIG. 9.

Figure 10:
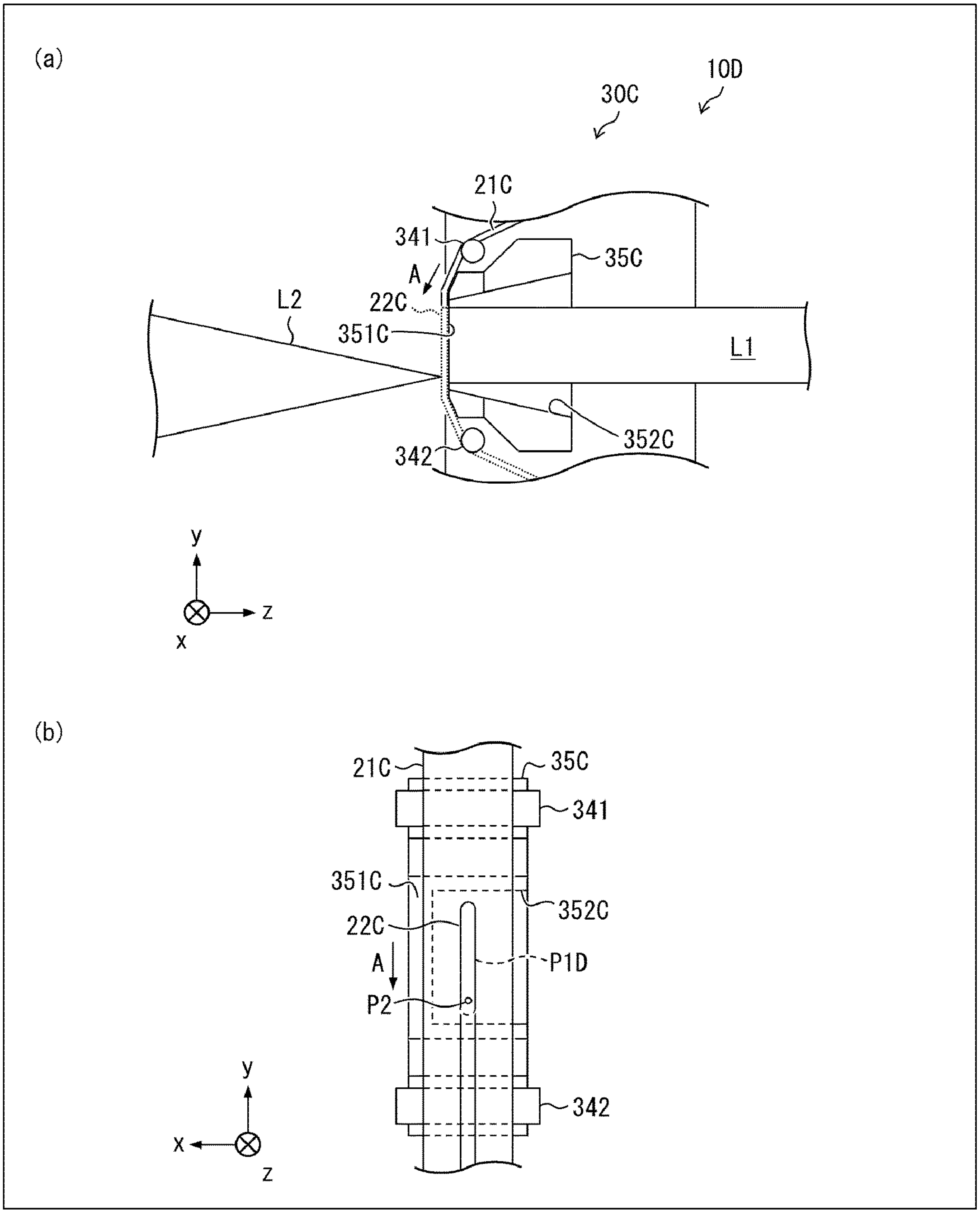

(a) of FIG. 10 is a side view of a continuous film-feed device of a carbon ion generating device in accordance with Embodiment 5 of the present invention. (b) of FIG. 10 is a plan view of a head surface of a tape head illustrated in (a) of FIG. 10.

Figure 11:
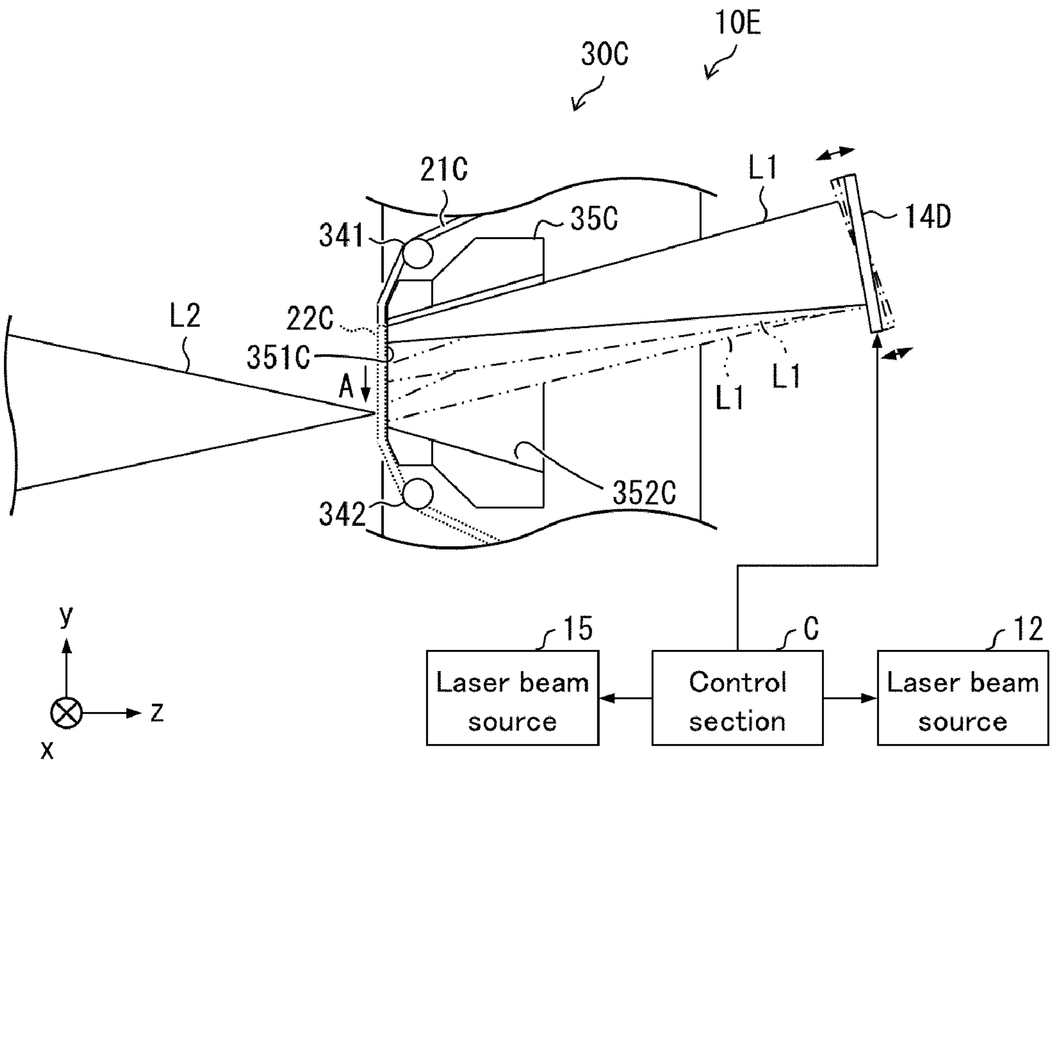

FIG. 11 is a side view of a continuous film-feed device of a carbon ion generating device in accordance with Embodiment 6 of the present invention.

DESCRIPTION OF EMBODIMENTS

Embodiment 1

The following description will discuss, with reference to FIG. 1, a carbon ion generating device 10 in accordance with Embodiment 1 of the present invention. (a) of FIG. 1 is a view schematically illustrating the carbon ion generating device 10. (b) of FIG. 1 is a cross-sectional view obtained by enlarging a carbonized region of a film that is used to generate carbon ions in the carbon ion generating device 10. The carbon ion generating device 10 can generate carbon ions ($C^{4+}$). The generated carbon ions can be used as, for example, carbon ions with which a tumor is irradiated in heavy ion cancer therapy.

<Carbon Ion Generating Device>

As illustrated in (a) of FIG. 1, the carbon ion generating device 10 includes a chamber 11, a laser beam source 12, a lens 13, a mirror 14, a laser beam source 15, and a focusing mirror 16.

(Chamber)

The chamber 11 is a container that is made of metal (stainless steel in Embodiment 1) and is cylindrical. In (a) of FIG. 1, a single solid line is used to simply illustrate a shape of the chamber 11. Note, however, that the chamber 11 actually has a thickness which is appropriately set.

The chamber 11 is configured so as to be able to close an internal space thereof. To the chamber 11, a vacuum pump (not illustrated in (a) of FIG. 1) is connected. The vacuum pump keeps a pressure in the internal space lower than an atmospheric pressure by evacuating the internal space of the chamber 11. In Embodiment 1, the pressure in the internal space of the chamber 11 is approximately $1\times10^{-2}$ Pa. Note, however, that the pressure in the internal space of the chamber 11 is not limited to the above pressure and can be set as appropriate.

As illustrated in (a) of FIG. 1, the chamber 11 is provided with two ports 111 and 112. Each of the ports 111 and 112 is a light input/output port and is made of a plate-like member that is made of glass which is quartz glass and that allows a corresponding one of laser beams L1 and L2 (described later) to be transmitted therethrough. As described later, the laser beam L1 has a center wavelength of 532 nm, and the laser beam L2 has a center wavelength of 810 nm. Note, however, that a material of which each of the ports 111 and 112 is made is not limited to quartz glass and may be any material that is light-transmissive from a visible region to an infrared region. In the following description, the center wavelengths of the laser beams L1 and L2 are also simply referred to as wavelengths of the laser beams L1 and L2.

(First Laser Beam Source)

The laser beam source 12 emits the laser beam L1. The wavelength and an output of the laser beam L1 are determined so that in-situ irradiation of a film 21, which is a film made of an organic compound, with the laser beam L1 in-situ carbonizes the organic compound, of which the film 21 is made, and generates a carbonized region 22. (b) of FIG. 1 illustrates only the carbonized region 22 of the film 21.

In Embodiment 1, the laser beam source 12 is a semiconductor laser that emits the laser beam L1 which has a wavelength of 532 nm. In Embodiment 1, the laser beam source 12 is set so that the laser beam L1 has an output of approximately 520 mW at a beam spot P1 (described later). Note, however, that the wavelength and the output of the laser beam L1 can be selected as appropriate provided that the organic compound of which the film 21 is made can be carbonized.

The laser beam source 12 and the laser beam L1 are examples of a first laser beam source and a first laser beam, respectively. The laser beam source 12 is disposed so that the laser beam L1 enters the internal space of the chamber 11 through the port 111.

Although not illustrated in (a) of FIG. 1, a collimating lens is provided downstream of the laser beam source 12. Thus, the collimating lens converts, into collimated light, the laser beam L1 that has been emitted from the laser beam source 12 and that is divergent light.

The lens 13 and the mirror 14 are provided on an optical axis of the laser beam L1 in the internal space of the chamber 11. The lens 13 converts, into convergent light, the laser beam L1 that is collimated light. The mirror 14 reflects the laser beam L1 so as to irradiate a partial region of one (the positive z-axis direction side main surface in (a) of FIG. 1) of main surfaces of the film 21 with the laser beam L1 that is convergent light. Thus, the partial region of the one of the main surfaces of the film 21 is irradiated, via the lens 13 and the mirror 14, with the laser beam L1 that has entered the internal space of the chamber 11 through the port 111. Note that the laser beam source 12, the lens 13, and the mirror 14 are an example of a first laser irradiation mechanism that carbonizes, by irradiation with the laser beam L1, a partial region of the film 21 which partial region has been irradiated with the laser beam L1. The beam spot P1 is an example of a region of the one of the main surfaces of the film 21 which region is irradiated with the laser beam L1. In Embodiment 1, the beam spot P1 has a diameter of approximately 300 μm and an area of 0.09 mm². Note that the lens 13 can be omitted in a case where the laser beam L1 has a sufficiently high output in order to carbonize the organic compound that is contained in the beam spot P1.

The optical axis of the laser beam L1 is inclined with respect to a direction (z-axis direction illustrated in FIG. 1) parallel to a normal of the film 21. In Embodiment 1, a first incident angle, which is an angle formed between the optical axis of the laser beam L1 and the normal of the film 21, is approximately 30'. Note, however, that the first incident angle is not limited to the above angle and can be set as appropriate. The first incident angle may be 0° (that is, the optical axis of the laser beam L1 may be parallel to the normal of the film 21).

The wavelength and the output of the laser beam L1, and the area of the beam spot P1 are preferably determined so that the film 21 at the beam spot P1 is heated to a temperature of not lower than 600° C. For example, in a case where the laser beam L1 has a wavelength of 532 nm and the beam spot P1 has an area of 0.09 mm², the laser beam L1 preferably has an output of not less than 360 mW at the beam spot P1. This configuration makes it possible to heat the film 21 at the beam spot P1 to a temperature of not lower than 600° C.

(Second Laser Beam Source)

The laser beam source 15 emits the laser beam L2. Irradiation of the film 21 with the laser beam L2 results in generation of carbon ions ($C^{4+}$) from the carbonized region 22. In Embodiment 1, the laser beam source 15 is a Ti:sapphire laser that emits the laser beam L2 which has a center wavelength of 810 nm and a pulse width of 80 fsec. In Embodiment 1, the laser beam source 15 and an optical axis of the laser beam L2 are set so that the laser beam L2 has energy per pulse of approximately 500 mJ and a beam spot P2 (described later) has a diameter of not less than 2 μm and not more than 3 μm. Thus, in Embodiment 1, the diameter of the beam spot P2 is not more than 1/100 times the diameter of the beam spot P1. Note, however, that the wavelength and the energy per pulse of the laser beam L2 can be selected as appropriate provided that the carbon ions can be generated from the carbonized region 22.

In Embodiment 1, the carbonized region 22 is formed by irradiating the beam spot P1 with the laser beam L1, and the beam spot P2 is irradiated with the laser beam L2 with the carbonized region 22 irradiated with the laser beam L1. That is, the carbonized region 22 is irradiated with the laser beam L1 together with the laser beam L2. This configuration makes it possible to secure sufficient time for carbonization of a polyimide resin contained in the beam spot P1. Note, however, that the carbonized region 22 need not be configured to be irradiated with the laser beam L1 together with the laser beam L2 and may be configured so that the carbonized region 22 is irradiated with the laser beam L1 and then irradiated with the laser beam L2. In this case, an irradiation interval, which is a time from irradiation with the laser beam L1 until irradiation with the laser beam L2, is preferably as short as possible. The irradiation interval is preferably not more than 5 seconds in a case where the pressure in the internal space of the chamber 11 is approximately $1\times10^{-2}$ Pa. A longer irradiation interval reduces an effect (i.e., removal of an impurity layer) associated with irradiation with the laser beam L1. Thus, the longer irradiation interval reduces the number and maximum energy of generated carbon ions and increases the number and maximum energy of generated hydrogen ions ($H^+$). The irradiation interval will be described later with reference to FIG. 4.

As illustrated in (a) of FIG. 1, the optical axis of the laser beam L2 is determined so that the beam spot P2 is included in the beam spot P1, and, more preferably, so that the beam spot P2 is substantially concentric with the beam spot P1. That is, the laser beam source 15 is configured to irradiate, with the laser beam L2, at least a part of the beam spot P1 which is being irradiated with the laser beam L1. The optical axis of the laser beam L2 may be adjusted while a high-magnification camera is used to observe the beam spot P1.

The laser beam source 15 and the laser beam L2 are examples of a second laser beam source and a second laser beam, respectively. The laser beam source 15 is disposed so that the laser beam L2 enters the internal space of the chamber 11 through the port 112.

Although not illustrated in (a) of FIG. 1, a collimating lens is provided downstream of the laser beam source 15. Thus, the collimating lens converts, into collimated light, the laser beam L2 that has been emitted from the laser beam source 15 and that is divergent light.

The focusing mirror 16 is provided on the optical axis of the laser beam L2 in the internal space of the chamber 11. By reflecting the laser beam L2 while converting, into convergent light, the laser beam L2 that is collimated light, the focusing mirror 16 irradiates, with the laser beam L2 that is convergent light, the beam spot P2 that is a part of the other (the negative z-axis direction side main surface in (a) of FIG. 1) of the main surfaces of the film 21. In Embodiment 1, the focusing mirror 16 is an off-axis parabolic mirror. Thus, the beam spot P2 that is a part of the other of the main surfaces of the film 21 is irradiated, via the focusing mirror 16, with the laser beam L2 which has entered the internal space of the chamber 11 through the port 112. Note that the laser beam source 15 and the focusing mirror 16 are an example of a second laser irradiation mechanism that generates carbon ions from the carbonized region 22 by irradiating at least a part of the carbonized region 22 with the laser beam L2. The beam spot P2 is an example of a region of the carbonized region 22 which region is irradiated with the laser beam L2.

In Embodiment 1, the optical axis of the laser beam L2 is inclined with respect to the direction (z-axis direction illustrated in FIG. 1) parallel to the normal of the film 21. In Embodiment 1, a second incident angle, which is an angle formed between the optical axis of the laser beam L2 and the normal of the film 21, is approximately 43°. Note, however, that the second incident angle is not limited to the above angle and can be set as appropriate. The second incident angle may be 0° (that is, the optical axis of the laser beam L2 may be parallel to the normal of the film 21).

(Film)

The film 21 as a whole including the beam spot P1 and the beam spot P2 is held in a planar manner by a holding section. A mechanism by which the holding section holds the film 21 is not limited and can be selected as appropriate. In FIG. 1, the holding section is not illustrated.

In Embodiment 1, the film 21 that is irradiated with the laser beam L1 and the laser beam L2 is a film that has a square shape and that is made of a polyimide resin. The film 21 is larger than beam spot P1 and the beam spot P2. In Embodiment 1, the film 21 has a thickness of 5 μm. Note, however, that the film 21 can have a shape which is not limited to the square shape and is selected as appropriate.

The polyimide resin is an example of the organic compound. The material of which the film 21 is made is not limited to the polyimide resin. Examples of another organic compound of which the film 21 is made include a polyester resin and a polypropylene resin.

The thickness of the film 21 is not limited to 5 μm and is preferably not less than 100 nm and not more than 12.5 μm. The thickness of the film 21 is preferably not less than 1 μm and not more than 5 μm.

The film 21 that has a smaller thickness enables carbon ions generated from the film 21 to have higher acceleration energy. Furthermore, the film 21 that has a thickness of not less than 100 nm, and more preferably not less than 1 μm makes it possible to prevent or reduce damage which may occur in the carbonized region 22. This ensures an interaction between the laser beam L2 and the carbonized region 22.

The one of the main surfaces of the film 21 may be laminated or coated with a reinforcing layer that reinforces a film made of an organic compound. The reinforcing layer is preferably a film that is made of a material which, as compared with an organic compound, has a higher strength when irradiated with the laser beam L1. Examples of such a material include metals (e.g., nickel, gold, etc.) having high surface chemical stability.

(Principle of Carbon Ion Generation)

In a case where the film 21 is irradiated with the laser beam L1, a color of the polyimide resin contained in the beam spot P1 is changed to black, and the carbonized region 22 is formed in a region including the beam spot P1. (b) of FIG. 1 is an enlarged view of a cross-section of the carbonized region 22 of the film 21, the cross-section including the beam spot P2 which is irradiated with the laser beam L2. Note that the diameter of the beam spot P1 is approximately 100 times as large as the diameter of the beam spot P2 as described earlier. Thus, the beam spot P1 is not illustrated in (b) of FIG. 1. In (b) of FIG. 1, the second incident angle, which is an angle formed between the optical axis of the laser beam L2 and the normal of the film 21, is 0°. Furthermore, in (b) of FIG. 1, the beam spot P2 and an ion generation region P3 are indicated by thick solid lines.

In the following description, of a pair of main surfaces constituting the carbonized region 22, a first main surface that is irradiated with the laser beam L2 is referred to as a front surface 221, and a second main surface on an opposite side from the front surface (in Embodiment 1, a main surface that is irradiated with the laser beam L1) is referred to as a back surface 222.

As illustrated in (b) of FIG. 1, in a case where the beam spot P2 included in the front surface 221 of the carbonized region 22 is irradiated with the laser beam L2, electrons that are present at or near the beam spot P2 of the carbonized region 22 vigorously vibrate due to an interaction occurring between the electrons and the laser beam L2, and are accelerated in a direction (positive z-axis direction in (b) of FIG. 1) from the front surface 221 toward the back surface 222, and are ejected from the ion generation region P3 of the back surface 222 to outside the carbonized region 22. In this case, the electrons that have been ejected from the back surface 222 to outside the carbonized region 22 generate a sheath electric field between the electrons and carbon ions remaining in the carbonized region 22. In (b) of FIG. 1, a range of a region in which the laser beam L2 propagates inside the carbonized region 22 is schematically illustrated by an imaginary line (two-dot chain line).

The carbon ions remaining in the carbonized region 22 are accelerated by the sheath electric field and ejected from the back surface 222 to outside the carbonized region 22. An energy distribution of the carbon ions that have been ejected from the carbonized region 22 can be measured with use of, for example, a Thomson parabola ion analyzer. In (b) of FIG. 1, a shape of a region in which the ejected carbon ions are distributed in a space that is located on the back surface 222 side of the carbonized region 22 is schematically indicated by an imaginary line (two-dot chain line).

The carbon ions that are ejected, as described above, from the back surface 222 that is the main surface on the opposite side from the front surface 221 which has been irradiated with the laser beam L2 are referred to as forward-accelerated ions. Furthermore, as disclosed in Phys. Rev. Lett. 99, 185002 (2007), it is known that carbon ions are ejected also from the front surface 221 in a case where the front surface 221 is irradiated with the laser beam L2 in which the ratio of background light (prepulses) to main pulses is small. The carbon ions that are thus ejected from the front surface 221 are referred to as backward-accelerated ions. Carbon ions with which a tumor is to be irradiated in heavy ion cancer therapy can be either the forward-accelerated ions or the backward-accelerated ions.

As described earlier, in a case where the film 21 is a film one of main surfaces of which is laminated or coated with a reinforcing layer, a main surface on which the reinforcing layer is to be provided may be determined in accordance with which of the forward-accelerated ions and the backward-accelerated ions will be used for therapy. For example, in a case where the forward-accelerated ions illustrated in (b) of FIG. 1 are used for the therapy, the reinforcing layer may be provided on the front surface 221 because the ions are ejected from the back surface 222. In contrast, in a case where the backward-accelerated ions are used for the therapy, the reinforcing layer may be provided on the back surface 222 because the ions are ejected from the front surface 221. Regardless of which of the main surfaces that are the front surface 221 and the back surface 222 has been irradiated with the laser beam L1, the laser beam L1 (i) carbonizes the film 21 that is included in the beam spot P1 and its vicinity, and (ii) removes impurity layers that are formed on the front surface 221 and the back surface 222, respectively. Thus, regardless of which of the forward-accelerated ions and the backward-accelerated ions are used for the therapy, either the front surface 221 or the back surface 222 may be irradiated with the laser beam L2.

Example 1 and Group of Examples 2

A case where the irradiation interval, which is a time from irradiation with the laser beam L1 until irradiation with the laser beam L2, was 0 second in the carbon ion generating device 10 (described earlier) is regarded as Example 1 of the present invention. Cases where the irradiation interval was 1 second, 5 seconds, 15 seconds, and 60 seconds in the carbon ion generating device 10 (described earlier) are regarded as Group of Examples 2 of the present invention. Cases where in the carbon ion generating device 10 (described earlier), irradiation with the laser beam L1 was not carried out and irradiation with only the laser beam L2 was carried out with respect to the beam spot P2 are regarded as a comparative example with respect to Example 1 and Group of Examples 2. In the following description, this comparative example is referred to as Comparative Example 1. Note that parameters other than the irradiation interval are as described earlier.

(a) and (b) of FIG. 2 are images showing energy distributions of ions generated with use of Comparative Example 1 and Example 1 of the present invention. In (a) and (b) of FIG. 2, the horizontal axis shows an index corresponding to energy of generated ions, and a light emission intensity represents an amount of the generated ions. A value which is closer to 0 mm on the horizontal axis means that the generated ions have greater energy.

FIG. 3 is a graph showing energy spectra of carbon ions generated with use of Comparative Example 1 and Example 1 of the present invention.

With reference to (a) and (b) of FIG. 2 and FIG. 3, as compared with a case of irradiation with only the laser beam L2, irradiation with the laser beam L1 together with the laser beam L2 showed a 3.4-fold increase in maximum energy of the carbon ions from 2.5 MeV to 8.5 MeV. Furthermore, irradiation with the laser beam L1 together with the laser beam L2 showed an approximately 20-fold increase in amount of the carbon ions generated. The amount of the carbon ions generated is obtained by integrating dI/dE in the graph illustrated in FIG. 3. It has also been found that irradiation with the laser beam L1 together with the laser beam L2 makes it possible not only to increase the amount of the carbon ions generated but also to prevent or reduce generation of hydrogen ions, which are impurity ions.

Images of FIG. 4 illustrate energy distributions of ions generated by Example 1 of the present invention and by a case where the irradiation interval was changed to 1 second, 5 seconds, 15 seconds, and 60 seconds in Group of Examples 2 of the present invention. The horizontal axis and the vertical axis in FIG. 4 are identical to the horizontal axis and the vertical axis, respectively, in (a) and (b) of FIG. 2.

With reference to FIG. 4, it has been found that ions generated by each of the examples of Group of Examples 2 include more carbon ions than in Comparative Example 1 (see (a) of FIG. 2) and that it is possible to prevent or reduce generation of hydrogen ions, which are impurity ions. However, it has been found that a longer irradiation interval causes the carbon ions to have a lower light emission intensity and causes a spectrum of the carbon ions to be shifted to the low energy side. It has also been found that a longer irradiation interval causes the hydrogen ions to have a higher light emission intensity and causes a spectrum of the hydrogen ions to be shifted to the high energy side. It has been determined from a result shown in FIG. 4 that Group of Examples 2 is not significantly different in result from Example 1 as long as the irradiation interval is not more than 5 seconds. That is, the irradiation interval is preferably not more than 5 seconds.

Example 3

A case where the irradiation interval, which is a time from irradiation with the laser beam L1 until irradiation with the laser beam L2, was 0 second in the carbon ion generating device 10 (described earlier) is regarded as Example 3 of the present invention. A case where in the carbon ion generating device 10 (described earlier), irradiation with the laser beam L1 was not carried out and irradiation with only the laser beam L2 was carried out with respect to the beam spot P2 is regarded as a comparative example with respect to Example 3. In the following description, this comparative example is referred to as Comparative Example 2. Example 3 is different from Example 1 in that in Example 3, the pulse width is 45 fsec, the energy per pulse of the laser beam L2 is approximately 8 J, and the beam spot diameter of the beam spot P2 is approximately 1.5 μm.

(a) and (b) of FIG. 5 are graphs showing depth dependence of composition ratios of films used in Comparative Example 2 and Example 3. In Comparative Example 2, in which irradiation with the laser beam L1 was not carried out, a material of which a film is made is unchanged from polyimide. In contrast, in Example 3, the carbonized region 22 was formed by irradiation with the laser beam L1. (b) of FIG. 5 shows a result of measurement of the depth dependence of a composition ratio of the carbonized region 22. The composition ratio was measured with use of X-ray photoelectron spectroscopy (XPS). The depth dependence of the composition ratio was determined as below. Specifically, in a chamber, gas cluster ion beams were used to mill a surface of the film by sputtering the surface, and measure XPS each time. An argon cluster was used as sputtered particles. A milling device used in Example 3 has an ability to mill, at a milling rate of 1.7 nm/min, a processing target object that is quartz glass.

With reference to (a) and (b) of FIG. 5, it has been found that polyimide was carbonized by irradiation with the laser beam L1 in Example 3. Specifically, a composition ratio of carbon inside the film 21, which composition ratio had been approximately 80% in Comparative Example 2, was increased to approximately 95% in Example 3.

It has also been found that oxygen, which is an impurity, was present on or near the surface of the film in each of Comparative Example 2 and Example 3. This oxygen is considered to be derived from water vapor ($H_2O$) remaining in the chamber. FIG. 5 does not illustrate a composition ratio of hydrogen because XPS is insufficient to detect hydrogen.

Thus, it has been found that irradiation with the laser beam L1 enables carbonization of polyimide, so that the composition ratio of carbon in the carbonized region 22 can be increased. It has also been found that, also in a case where the laser beam L1 was used to form the carbonized region 22 as in Example 3, an impurity gas (mainly water vapor) was present on a surface of the carbonized region 22. Thus, it has been found that, in order to increase purity of carbon ions to be generated, it is preferable to employ a configuration which makes it possible to remove an impurity gas while forming a carbonized region 22A, as described later in and after Embodiment 4.

(a) and (c) of FIG. 6 are images showing energy distributions of ions generated with use of Comparative Example 2 and Example 3. The horizontal axis and the vertical axis in (a) and (c) of FIG. 6 are, at full scale, 70 mm and 65 mm, respectively. In Comparative Example 2, carbon ions were generated in a small amount. Thus, an accumulation of measurement results in the case of 20-shot irradiation with the laser beam L2 is illustrated. (b) and (d) of FIG. 6 are graphs showing energy spectra of ions generated with use of Comparative Example 2 and Example 3.

With reference to (a) to (d) of FIG. 6, as compared with the case of irradiation with only the laser beam L2, irradiation with the laser beam L2 during a period of irradiation with the laser beam L1 showed an approximately 3-fold increase in maximum energy of carbon ions from approximately 4 MeV to approximately 10.7 MeV. It has also been found that irradiation with the laser beam L1 together with the laser beam L2 makes it possible not only to increase the amount of the carbon ions generated but also to prevent or reduce generation of hydrogen ions, which are impurity ions.

Embodiment 2

The following description will discuss, with reference to FIG. 7, a continuous film-feed device 30 of a carbon ion generating device 10A in accordance with Embodiment 2 of the present invention. (a) of FIG. 7 is a side view of the continuous film-feed device 30. (b) of FIG. 7 is a plan view of a head surface 351 of a variation of a tape head 35 of the continuous film-feed device 30. Note that for convenience, members having functions identical to those of the respective members described in Embodiment 1 are given respective identical reference numerals, and a description of those members is omitted.

The carbon ion generating device 10 in accordance with Embodiment 1 is configured so that the holding section is used to hold, in a planar manner, the film 21 which is square.

In contrast, the carbon ion generating device 10A includes, in place of the film 21 and the holding section of the carbon ion generating device 10, a film 21A that is formed in a form of a tape and a continuous film-feed device 30 that continuously feeds the film 21A in a longer side direction of the film 21A. The carbon ion generating device 10A further includes a control section C. In Embodiment 2, the film 21A, the continuous film-feed device 30, and the control section C will be described.

<Film>

The film 21A is formed in the form of a tape. The film 21A has one end that is fixed to a core which is a hollow cylinder. The film 21A the one end of which is fixed to the core is wound on the core. The film 21A has a larger width than a first region that is irradiated with a laser beam L1 and a second region that is irradiated with a laser beam L2.

Except for this point, the film 21A is configured as in the case of the film 21. That is, the film 21A is made of a polyimide resin and has a thickness of 5 μm. A material of which the film 21A is made not limited to the polyimide resin, and the thickness is not limited to 5 μm.

<Continuous Film-Feed Device>

The continuous film-feed device 30 is provided inside the chamber 11 in place of the holding section of the carbon ion generating device 10. However, the continuous film-feed device 30 includes a holding section and a movement section as described later.

As illustrated in (a) of FIG. 7, the continuous film-feed device 30 includes pulleys 311, 312, 321, 322, 331, 332, 341, and 342, the tape head 35, motors 361 and 362, and a base material 37.

(Base Material)

The base material 37 is a plate-like member which is made of metal (stainless steel in Embodiment 2) and a pair of main surfaces of which has a rectangular shape. The pulleys 311, 312, 321, 322, 331, 332, 341, and 342, the tape head 35, and the motors 361 and 362 are provided on one of the main surfaces of the base material 37. Although not illustrated in FIG. 7, a stage that makes it possible to translate a position of the base material 37 at least in the z-axis direction may be provided below the base material 37.

(Pulley)

The pulley 311 includes a rotating shaft that is configured so as to be rotatable. To the rotating shaft, a core (hereinafter referred to as a first core) is fixed on which one end of the film 21A is wound. Thus, the first core can rotate together with the pulley 311.

In Embodiment 2, the other end of the film 21A is fixed to a second core that is a hollow cylinder.

As in the case of the pulley 311, the pulley 312 includes a rotating shaft that is configured so as to be rotatable. To the rotating shaft, the second core is fixed on which the other end of the film 21A is wound. Thus, the second core can rotate together with the pulley 312.

The pulleys 321, 322, 331, 332, 341, and 342 are provided between the pulley 311 and the pulley 312 and define a path of the film 21A from the pulley 311 to the pulley 312 (see (a) of FIG. 7). As in the case of the pulleys 311 and 312, the pulleys 321, 322, 331, 332, 341, and 342 also include respective rotating shafts each of which is configured so as to be rotatable.

In Embodiment 2, the pulleys 311, 321, 331, and 341 and the pulleys 312, 322, 332, and 342 are provided so as to be in reflection symmetry with a plane parallel to a zx plane illustrated in (a) of FIG. 7 as a symmetry plane.

The pulleys 311, 312, 321, 322, 331, 332, 341, and 342 thus configured enable the film 21A to be continuously fed along an arrow A from the pulley 311 to the pulley 312. Thus, the pulley 311 is an example of a first pulley through which the film 21A is fed, and the pulley 312 is an example of a second pulley around which the film 21A is wound.

(Tape Head)

The tape head 35 is a block-like member that is made of metal (stainless steel in Embodiment 2). When viewed in a direction normal to the main surfaces of the base material 37, the tape head 35 is formed in a shape of a decagon obtained by combining two large and small hexagons (see (a) of FIG. 7). A pair of surfaces of the tape head 35 which surfaces are substantially parallel to the main surfaces of the base material 37, the tape head 35 being formed in the shape of a decagon as described above, is referred to as a pair of main surfaces, and surfaces of the tape head 35 which surfaces constitute contours of the pair of main surfaces are referred to as outer surfaces.

The tape head 35 is located between the pulley 311 and the pulley 312 when viewed along the path of film 21A. More specifically, the tape head 35 is provided so that a smaller hexagon of the two large and small hexagons (described earlier) is positioned between the pulley 341 and the pulley 342, and a part of the smaller hexagon protrudes from the negative z-axis direction side circumscribed surface of a circumscribed surface which is circumscribed about the pulleys 341 and 342. Thus, the head surface 351, which is at least the negative z-axis direction side end surface of the outer surfaces of the tape head 35, comes into contact with the film 21A that is extruded from the negative z-axis direction side circumscribed surface (described above) in the negative z-axis direction.

Note that the tape head 35 can adjust its position in a direction of an arrow B which direction is parallel to the z-axis direction. Thus, the tape head 35 can arbitrarily adjust an amount in which the head surface 351 protrudes from the negative z-axis direction side circumscribed surface (described earlier). In other words, the tape head 35 can use the head surface 351 to determine the position in the direction normal to the main surfaces of the film 21A (in the z-axis direction in (a) of FIG. 7). Thus, the head surface 351 is an example of the holding section that holds the film 21A in a planar manner at a beam spot P1 and a beam spot P2.

A groove 352 is formed on a main surface (negative x-axis direction side main surface) of the pair of main surfaces of the tape head 35 which main surface is farther from the base material 37. The groove 352 has a trapezoidal shape when viewed in the direction normal to the main surfaces of the base material 37. A pair of bases of the groove 352 are located on the positive z-axis direction side edge and the negative z-axis direction side edge, respectively, of the contours of the tape head 35. That is, the positive z-axis direction side end surface and the head surface 351 of the outer surfaces of the tape head 35 are provided with respective notches, which are connected by the groove 352.

The groove 352 extends from the positive z-axis direction side end surface to the head surface 351 of the outer surfaces of the tape head 35. An optical axis of the laser beam L1 is set so as to pass through an inside of the groove 352. Thus, on the head surface 351, the partial region of the film 21A is irradiated with the laser beam L1 that has passed through the inside of the groove 352.

Note that at least a partial region of a carbonized region 22A is irradiated with the laser beam L2 during the period of irradiation with the laser beam L1 also in the carbon ion generating device 10A as in the case of the carbon ion generating device 10 (see (a) of FIG. 7).

In Embodiment 2, a first incident angle and a second incident angle are both 0°. Note, however, that each of the first incident angle and the second incident angle is not limited to 0° and can be set as appropriate. Note also that carbon ions with which a tumor is to be irradiated in heavy ion cancer therapy can be either forward-accelerated ions or backward-accelerated ions also in the carbon ion generating device 10A as in the case of the carbon ion generating device 10.

(Motor)

In Embodiment 2, the motors 361 and 362 are stepping motors. The motor 361 includes a rotating shaft that is configured so as to be rotatable. The rotating shaft of the motor 361 is mechanically coupled to the rotating shaft of the pulley 311. The motor 362 has a configuration similar to the configuration of the motor 361, and the rotating shaft of the motor 362 is mechanically coupled to the rotating shaft of the pulley 312. Thus, rotation of the rotatable shafts of the motors 361 and 362 drives the respective pulleys 311 and 312.

In Embodiment 2, the motors 361 and 362 are controlled by the control section C (see (a) of FIG. 7) of the carbon ion generating device 10A. The control section C drives the pulleys 311 and 312 by controlling the motors 361 and 362, and feeds the film 21A from the pulley 311 to the pulley 312. The motors 361 and 362 and the pulleys 311 and 312 are an example of the movement section.

(Timing of Irradiation with Light)

In Embodiment 2, after stopping feed of the film 21A (i.e., stopping the motors 361 and 362), the control section C forms the carbonized region 22A by irradiating the partial region of the film 21A with the laser beam L1, and then irradiates the partial region of the carbonized region 22A with the laser beam L2 with the carbonized region 22A irradiated with the laser beam L1. That is, the carbonized region 22A is irradiated with the laser beam L1 together with the laser beam L2. This configuration makes it possible to secure sufficient time for carbonization of a polyimide resin contained in a region of the film 21A which region is irradiated with the laser beam L1. Note, however, that the carbonized region 22 need not be configured to be irradiated with the laser beam L1 together with the laser beam L2 and may be configured so that the carbonized region 22 is irradiated with the laser beam L1 and then irradiated with the laser beam L2. In this respect, the carbon ion generating device 10A is similar to the carbon ion generating device 10.

In a case where the laser beam L1 has an output that is so sufficiently high as to quickly carbonize the polyimide resin of which the film 21A is made, the control section C may be configured to irradiate the film 21A with the laser beam L1 and the laser beam L2 while feeding the film 21A (i.e., with the pulleys 311 and 312 driven with use of the motors 361 and 362).

In this case, as in the variation illustrated in (b) of FIG. 7, the head surface 351 of the tape head 35 preferably has a length (length in a direction of the arrow A) that is extended in the direction of the arrow A (a y-axis direction illustrated in (b) of FIG. 7), in which direction the film 21A is fed. This configuration makes it possible for the beam spot P1 (a region that is irradiated with the laser beam L1 in (b) of FIG. 7) and the beam spot P2 (a region that is irradiated with the laser beam L2 in (b) of FIG. 7) to be different in position in a plane of the head surface 351. With the beam spot P1 and the beam spot P2 different in position, the motors 361 and 362 and the pulleys 311 and 312 continue to move the film 21A in the direction of the arrow A so that the carbonized region 22A obtained by carbonization at the beam spot P1 overlaps a position of the beam spot P2. This enables the carbon ion generating device 10A to generate carbon ions while feeding the film 21A.

<Control Section>

The control section C controls the motors 361 and 362 as described earlier. The control section C also controls a laser beam source 12 that emits the laser beam L1 and a laser beam source 15 that emits the laser beam L2.

A function of the control section C can be realized by a program for causing a computer to function as the control section C. In this case, the control section C includes, as hardware for executing the program, a computer that has at least one control device (e.g., a processor) and at least one storage device (e.g., a memory). Use of the at least one control device and the at least one storage device to execute the program allows the control section C to control the motors 361 and 362, the laser beam source 12, and the laser beam source 15.

Embodiment 3

The following description will discuss, with reference to FIG. 8, a continuous film-feed device 40 of a carbon ion generating device 10B in accordance with Embodiment 3 of the present invention. (a) of FIG. 8 is a plan view of the continuous film-feed device 40. (b) of FIG. 8 is a cross-sectional view of a rotational movement stage 41 of the continuous film-feed device 40. Note that for convenience, members having functions identical to those of the respective members described in Embodiments 1 and 2 are given respective identical reference numerals, and a description of those members is omitted.

The continuous film-feed device 30 of the carbon ion generating device 10A in accordance with Embodiment 2 is configured to continuously feed the film 21A, which is formed in the form of a tape, in the longer side direction of the film 21A.

In contrast, the continuous film-feed device 40 of the carbon ion generating device 10B is configured to use, in place of the film 21A, a film 21B that is formed in, for example, a circular shape to continuously feed the film 21B by rotationally moving the film 21B in a plane (plane parallel to an xy plane in (a) of FIG. 8) of a main surface of the film 21B. In Embodiment 3, the film 21B and the continuous film-feed device 40 will be described.

<Film>

The film 21B is formed in the circular shape in Embodiment 3. Note, however, that the film 21B can have a shape which is not limited to the circular shape and is determined as appropriate. The film 21B may have, for example, a polygonal shape. In Embodiment 3, the film 21B has a diameter that is substantially identical to an outer diameter of an inner region of a stage body 4111 of the rotational movement stage 41 (described later), and the film 21B is larger than a first region that is irradiated with a laser beam L1 and a second region that is irradiated with a laser beam L2.

Except for this point, the film 21B is configured as in the case of the film 21. That is, the film 21B is made of a polyimide resin and has a thickness of 5 μm. A material of which the film 21B is made not limited to the polyimide resin, and the thickness is not limited to 5 μm.

<Continuous Film-Feed Device>

The continuous film-feed device 40 is disposed inside a chamber 11 in place of the continuous film-feed device 30 of the carbon ion generating device 10A.

As illustrated in (a) of FIG. 8, the continuous film-feed device 40 includes the rotational movement stage 41 and a horizontal movement stage 42.

(Rotational Movement Stage)

As illustrated in (a) and (b) of FIG. 8, the rotational movement stage 41 includes a stage 411, a cross-roller ring 412, a fastener 413, a base material 414, a motor 415, a pulley 416, and a belt 417.

The stage 411 includes the stage body 4111 that is made of metal (stainless steel in Embodiment 3) and a back plate 4112. The stage body 4111 is a cylindrical member that has a pair of bottom surfaces each of which is provided with a circular opening and a side surface which is interposed between the pair of bottom surfaces. Thus, a region of the stage body 4111 which region includes a central axis AC is provided with a through-hole (see (b) of FIG. 8).

In the stage body 4111, a vicinity of one (the negative z-axis direction side bottom surface illustrated in (a) and (b) of FIG. 8) of the pair of bottom surfaces is configured in a flange shape having a thicker side surface, as compared with a vicinity of the other (the positive z-axis direction side bottom surface illustrated in (a) and (b) of FIG. 8) of the pair of bottom surfaces. A groove 4113 is provided on an outer circumference of a flange-shaped part. The belt 417 (described later) is placed on the groove 4113. Note that the belt 417 is not illustrated in (b) of FIG. 8.

Furthermore, the inner region of the one of the pair of bottom surfaces of the stage body 4111, the inner region being ring-shaped and located further inward than the groove 4113, has a surface that is further dug down than a surface of the other region of the one of the pair of bottom surfaces. That is, a difference in level is provided at a boundary between the inner region and the other region on the one of the pair of bottom surfaces. The fastener 413 (described later) is used to fix, to the inner region, the film 21B that has an outer diameter which is substantially equal to the outer diameter of the inner region and that is formed in the circular shape.

The back plate 4112 is a circular ring-shaped plate-like member that is fixed to the other of the pair of bottom surfaces of the stage body 4111. An inner ring of the cross-roller ring 412 is fitted on or near the other of the pair of the bottom surfaces of the stage body 4111. The back plate 4112 and the stage body 4111 between which the cross-roller ring 412 is sandwiched fix the inner ring of the cross-roller ring 412 to the other of the pair of bottom surfaces.

The fastener 413 is a plate-like member that is made of metal (stainless steel in Embodiment 3) and that is circular ring-shaped. The fastener 413 is configured to have an outer diameter that is slightly smaller than the outer diameter of the inner region of the stage body 4111 and an inner diameter that substantially coincides with a diameter of the through-hole of the stage 411. The fastener 413 is fitted in the inner region.

As illustrated in (b) of FIG. 8, the fastener 413 and the stage body 4111 between which the film 21B is sandwiched fix the film 21B to the inner region. Although not illustrated in (a) and (b) of FIG. 8, a mechanical fixing means is used to fix the fastener 413 to the stage 411. An example of the mechanical fixing means is a plurality of bolts. Note, however, that the mechanical fixing means is not limited to the above example and can be selected as appropriate.

The base material 414 includes a base material body 4141 that is made of metal (stainless steel in Embodiment 3) and a back plate 4142 (see (b) of FIG. 8). The base material body 4141 is a plate-like member a pair of main surfaces of which has a shape obtained by combining a rectangular shape and a circular shape (see (a) of FIG. 8). When the main surfaces of the base material body 4141 are viewed in a plan view from the negative z-axis direction side, an opening that is concentric with a circular contour is provided in a circular region. The opening has a diameter that is more than an outer diameter of the other of the pair of bottom surfaces of the stage body 4111 and slightly less than an outer diameter (diameter of an outer ring) of the cross-roller ring 412. To the opening, a part including the other of the pair of bottom surfaces of the stage body 4111 is fixed via the cross-roller ring 412.

The back plate 4142 is a circular ring-shaped plate-like member that is fixed to the circular region of the base material body 4141. The outer ring of the cross-roller ring 412 is fitted in the opening of the base material body 4141. The back plate 4142 and the base material body 4141 between which the cross-roller ring 412 is sandwiched fix the outer ring of the cross-roller ring 412 to the opening of the base material body 4141.

The cross-roller ring 412 is an aspect of a roller ring and is a bearing that includes an inner ring and an outer ring which are configured so as to be relatively rotatable. In the continuous film-feed device 40, the outer ring is fixed to the base material body 4141, and the stage body 4111 is fixed to the inner ring. The film 21B is fixed to the inner region of the stage body 4111 so that the main surface of the film 21B is parallel to the pair of bottom surfaces of the stage body 4111. Thus, the continuous film-feed device 40 rotationally moves the film 21B on the central axis AC in a plane (plane parallel to the xy plane illustrated in (a) of FIG. 8) of the main surface of the film 21B. The stage body 4111 and the fastener 413 are an example of a holding section that holds the film 21B in a planar manner at a beam spot P1 and a beam spot P2. The stage body 4111 and the fastener 413 between which an outer edge of the film 21B is sandwiched hold a plurality of parts of the outer edge.

The pulley 416 is provided on the negative z-axis direction side main surface in a rectangular region of the base material body 4141. The pulley 416 includes a rotating shaft that is configured so as to be rotatable. The rotating shaft of the pulley 416 is supported by the base material body 4141.

The motor 415 is fixed to the positive z-axis direction side main surface in the rectangular region of the base material body 4141. In Embodiment 3, the motor 415 is a stepping motor. The motor 415 includes a rotating shaft that is configured so as to be rotatable. The rotating shaft of the motor 415 is mechanically coupled to the rotating shaft of the pulley 416. Thus, rotation of the rotating shaft of the motor 415 results in rotation of the pulley 416.

The belt 417 is a circular ring-shaped member that is made of an elastic resin (rubber in Embodiment 3). The belt 417 is placed on an outer edge part of the pulley 416 and the groove 4113 of the stage 411. A length of the belt 417 is determined so that moderate tension is applied in a state in which the belt 417 is placed on the outer edge part and the groove 4113. The belt 417 transmits driving force of the motor 415 to the stage 411. Thus, in a case where the belt 417 is fed in a direction of an arrow A by rotation of the pulley 416, the stage 411 rotates in a direction of an arrow B (see (a) of FIG. 8).

Note that a further pulley may be provided between the pulley 416 and the stage 411 on the negative z-axis direction side main surface of the base material body 4141. In this case, the further pulley is provided at a position that causes a path of the belt 417 to slightly meander. The further pulley is configured so that a meandering state of the belt 417 can be adjusted. In the continuous film-feed device 40, use of the further pulley to adjust the meandering state makes it possible to adjust tension of the belt 417 and consequently to adjust a degree of friction between the belt 417 and each of the pulley 416 and the stage 411.

In Embodiment 3, the motor 415 is controlled by a control section C (see (a) of FIG. 8) of the carbon ion generating device 10B. The control section C controls the motor 415 so as to rotate the stage 411 of the rotational movement stage 41 via the pulley 416 and the belt 417. In other words, the control section C rotationally moves the film 21B in an in-plane direction of the main surface of the film 21B (an in-plane direction of the plane parallel to the xy plane illustrated in (a) of FIG. 8). Thus, the stage 411, the cross-roller ring 412, the motor 415, the pulley 416, and the belt 417 of the rotational movement stage 41 are an example of a movement section. Since the control section C of the carbon ion generating device 10B only needs to be configured as in the case of the control section C of the carbon ion generating device 10A, a description thereof is omitted in Embodiment 3.

In the carbon ion generating device 10 (see FIG. 1), the film 21 is irradiated with the laser beam L1 and the laser beam L2 from the respective different main surface sides of the film 21. In this respect, the carbon ion generating device 10A (see FIG. 7) is similar to the carbon ion generating device 10.

In contrast, in the carbon ion generating device 10B, the film 21B is irradiated with the laser beam L1 and the laser beam L2 from the same main surface side (negative z-axis direction side in (a) of FIG. 8) of the film 21B.

Thus, in an aspect of the present invention, a film can be irradiated with the laser beam L1 and the laser beam L2 from respective different main surface side of the film or from the same main surface side of the film.

Note that at least a partial region of a carbonized region 22B is irradiated with the laser beam L2 during a period of irradiation with the laser beam L1 also in the carbon ion generating device 10B as in the case of the carbon ion generating devices 10 and 10A (see (a) of FIG. 8).

Also in the carbon ion generating device 10B, each of a first incident angle and a second incident angle can be set as appropriate. Note also that carbon ions with which a tumor is to be irradiated in heavy ion cancer therapy can be either forward-accelerated ions or backward-accelerated ions also in the carbon ion generating device 10B as in the case of the carbon ion generating device 10. In the continuous film-feed device 40, not only the backward-accelerated ions but also the forward-accelerated ions can be used because the stage 411 is provided with the through-hole.

(Timing of Irradiation with Light)

In Embodiment 3, after stopping feed of the film 21B (i.e., stopping the motor 415), the control section C forms the carbonized region 22B by irradiating a partial region of the film 21B with the laser beam L1, and then irradiates at least the partial region of the carbonized region 22B with the laser beam L2 with the carbonized region 22B irradiated with the laser beam L1. That is, the carbonized region 22B is irradiated with the laser beam L1 together with the laser beam L2. This configuration makes it possible to secure sufficient time for carbonization of a polyimide resin contained in a region of the film 21B which region is irradiated with the laser beam L1. Note, however, that the carbonized region 22 need not be configured to be irradiated with the laser beam L1 together with the laser beam L2 and may be configured so that the carbonized region 22 is irradiated with the laser beam L1 and then irradiated with the laser beam L2.

In a case where the laser beam L1 has an output that is so sufficiently high as to quickly carbonize the polyimide resin of which the film 21B is made, the control section C may be configured to irradiate the film 21B with the laser beam L1 and the laser beam L2 while feeding the film 21B (i.e., with the rotational movement stage 41 rotated with use of the motor 415). In this case, a region that is irradiated with the laser beam L1 and a region that is irradiated with the laser beam L2 may be different in position in a main surface of the stage 411 to which main surface the film 21B is fixed.

In these respects, the carbon ion generating device 10B is similar to the carbon ion generating devices 10 and 10A.

(Horizontal Movement Stage)

The horizontal movement stage 42 includes a base material 421 and a stage 422 as illustrated in (a) of FIG. 8. The horizontal movement stage 42 can translate, in a plane (plane parallel to a zx plane illustrated in (a) of FIG. 8) of a main surface of the base material 421, a position of the stage 422 that is provided upright with respect to the base material 421. That is, the horizontal movement stage 42 can move the position of the stage 422 in each of an x-axis direction and a z-axis direction. The horizontal movement stage 42 can be a precision stage that is used to assemble an optical system and that enables translation of a stage in a plane.

In Embodiment 3, the position of the stage 422 is controlled by the control section C of the carbon ion generating device 10B. The control section C translates, in a plane, the rotational movement stage 41 that is fixed on the stage 422. Thus, the horizontal movement stage 42 is an example of the movement section.

As described above, translation of the rotational movement stage 41 by the horizontal movement stage 42 enables the carbon ion generating device 10B to arbitrarily change a radius R, which is an interval between (a) a region that is irradiated with the laser beam L1 and the region the laser beam L2 and (b) the central axis AC of the stage body 4111, without scanning each of the laser beam L1 and the laser beam L2.

In Embodiment 3, as illustrated in (a) of FIG. 8, a step of generating carbon ions and a step of rotating the stage 411 of the rotational movement stage 41 by a predetermined angle are alternately carried out in a state in which the horizontal movement stage 42 is fixed (i.e., the radius R is constant). This results in discontinuous formation of a plurality of carbonized regions 22B on a circumference of a circle in the film 21B.

However, as described earlier, in a case where the laser beam L1 has an output that is so sufficiently high as to quickly carbonize the polyimide resin of which the film 21B is made, the step of generating carbon ions may be carried out while the film 21B is being fed by rotating the stage 411. In this case, a carbonized region 22B that is circular ring-shaped is formed in the film 21B. Alternatively, the step of generating carbon ions may be carried out while the film 21B is being fed by rotating the stage 411 while translating the stage 422 in the x-axis direction. In this case, the carbonized region 22B that is spiral is formed in the film 21B.

Embodiment 4

The following description will discuss, with reference to FIG. 9, a continuous film-feed device 30C of a carbon ion generating device 10C in accordance with Embodiment 4 of the present invention and a laser beam L1 used in the carbon ion generating device 10C. (a) of FIG. 9 is a side view of the continuous film-feed device 30C. (b) of FIG. 9 is a plan view of a head surface 351C of a tape head 35C of the continuous film-feed device 30C. The carbon ion generating device 10C can also be referred to as a variation of the carbon ion generating device 10A illustrated in (a) and (b) of FIG. 2. Note that for convenience, members having functions identical to those of the respective members described in Embodiments 1 and 2 are given respective identical reference numerals, and a description of those members is omitted.

The carbon ion generating device 10A in accordance with Embodiment 2 is configured to use a single laser beam L1 to heat the film 21A so as to generate the carbonized region 22A in a part of the film 21A.

In contrast, the carbon ion generating device 10C uses three sub laser beams L11, L12, and L13 to constitute the laser beam L1, and beam spots P11, P12, and P13 which are irradiation regions of a film 21C which irradiation regions are irradiated with the respective sub laser beams L11, L12, and L13 are provided in a feed direction (direction of an arrow A illustrated in (b) of FIG. 9) in which the film 21C is fed. Thus, a first laser irradiation mechanism of the carbon ion generating device 10C includes three laser beam sources that emit the respective sub laser beams L11, L12, and L13. Each of these three laser beam sources is configured as in the case of the laser beam source 12 illustrated in (a) of FIG. 1 and (a) of FIG. 7. In the tape head 35C, in order to provide the beam spots P11, P12, and P13 in the feed direction in which the film 21C is fed, a groove 352C that is provided in the tape head 35C is further widened in the feed direction than the groove 352 of the tape head 35 illustrated in (a) of FIG. 7.

In the carbon ion generating device 10C, power densities of the sub laser beams L11, L12, and L13 at the respective beam spots P11, P12, and P13 are determined so as to increase from upstream to downstream in the feed direction in which the film 21C is fed (that is, the direction of the arrow A illustrated in (b) of FIG. 9).

This configuration enables temperatures of a carbonized region 22C at the respective beam spots P11, P12, and P13 to be gradually increased from upstream to downstream. For example, power of the sub laser beam L11 and a spot diameter of the beam spot P11 can be set so that the temperature of the carbonized region 22C at the beam spot P11 is 600° C., power of the sub laser beam L12 and a spot diameter of the beam spot P12 can be set so that the temperature of the carbonized region 22C at the beam spot P12 is 800° C., and power of the sub laser beam L13 and a spot diameter of the beam spot P13 can be set so that the temperature of the carbonized region 22C at the beam spot P13 is 1000'C.

However, the temperatures of the carbonized region 22C at the respective beam spots P11, P12, and P13 are not limited to 600° C., 800° C., and 1000° C. The temperature of the carbonized region 22C at the beam spot P11 only needs to be set to a temperature (for example, 500° C. or higher) at which at least a part of the film 21C is carbonized. The temperature of the carbonized region 22C at the beam spot P12 only needs to be set in a temperature region ranging from a temperature higher than the temperature of the carbonized region 22C at the beam spot P11 to a temperature lower than a melting point of carbon (approximately 4000 K in a case where, for example, the carbon is graphite). The temperature of the carbonized region 22C at the beam spot P13 only needs to be set in a temperature region ranging from a temperature higher than the temperature of the carbonized region 22C at the beam spot P12 to a temperature lower than a melting point of carbon (approximately 4000 K in a case where, for example, the carbon is graphite).

In the carbon ion generating device 10C, the power densities of the sub laser beams L11, L12, and L13 at the respective beam spots P11, P12, and P13 may be determined so as to be equal.

In Embodiment 4, a beam spot P2 that is a irradiation region of the film 21C which irradiation region is irradiated with a laser beam L2 is set so as to be included in the beam spot P13 (see (b) of FIG. 9). This configuration enables the beam spot P13 of the laser beam L13 to be irradiated with the laser beam L2 during a period in which the carbonized region 22C is irradiated with the laser beam L13. Note, however, that the beam spot P2 may be set so as to be located further downstream of the beam spot P13. In this case, an interval between the beam spot P13 and the beam spot P2 is preferably as short as possible in order to prevent or reduce adhesion of an impurity gas to the carbonized region 22C that has been irradiated with the laser beam L13.

Embodiment 5

The following description will discuss, with reference to FIG. 10, a continuous film-feed device 30C of a carbon ion generating device 10D in accordance with Embodiment 5 of the present invention and a laser beam L1 used in the carbon ion generating device 10D. (a) of FIG. 10 is a side view of the continuous film-feed device 30C. (b) of FIG. 10 is a plan view of a head surface 351C of a tape head 35C of the continuous film-feed device 30C. The carbon ion generating device 10D can also be referred to as a variation of the carbon ion generating device 10A illustrated in (a) and (b) of FIG. 2. Note that for convenience, members having functions identical to those of the respective members described in Embodiments 1 and 2 are given respective identical reference numerals, and a description of those members is omitted.

In the carbon ion generating device 10A in accordance with Embodiment 2, the first laser irradiation mechanism is configured so that the beam spot P1 that is the irradiation region of the film 21A which irradiation region is irradiated with the laser beam L1 has a circular shape.

In contrast, in the carbon ion generating device 10D, a first laser irradiation mechanism is configured so that a beam spot P1D that is an irradiation region of a film 21C which irradiation region is irradiated with the laser beam L1 has an oblong shape a major axis of which is parallel to a feed direction in which the film 21C is fed and a minor axis of which is parallel to a width direction of the film 21C (see (a) and (b) of FIG. 10). That is, in the carbon ion generating device 10D, the beam spot P1D is configured so that a length in the feed direction in which the film 21C is fed is longer than a direction orthogonal to the feed direction.

In Embodiment 5, a beam spot P2 that is an irradiation region of the film 21C which irradiation region is irradiated with a laser beam L2 is set so as to be included in the beam spot P1D that has the oblong shape (see (b) of FIG. 10). This configuration enables the beam spot P1D of the laser beam L1 to be irradiated with the laser beam L2 during a period in which a carbonized region 22C is irradiated with the laser beam L1. In this case, the beam spot P2 is preferably provided as downstream as possible (on the negative y-axis direction side) of a range of the beam spot P1D. This configuration enables the carbonized region 22C that has been irradiated with the laser beam L1 over a long period of time to be irradiated with the laser beam L2.

Note, however, that the beam spot P2 may be set so as to be located further downstream of the range of the beam spot P1D. In this case, a shortest distance between the beam spot P1D and the beam spot P2 is preferably as short as possible in order to prevent or reduce adhesion of an impurity gas to the carbonized region 22C that has been irradiated with the laser beam L1.

Embodiment 6

The following description will discuss, with reference to FIG. 11, a continuous film-feed device 30C and a galvanometer mirror 14D of a carbon ion generating device 10E in accordance with Embodiment 6 of the present invention and a laser beam L1 used in the carbon ion generating device 10E. FIG. 11 is a side view of the continuous film-feed device 30C. The carbon ion generating device 10E can also be referred to as a variation of the carbon ion generating device 10C illustrated in (a) and (b) of FIG. 9. Note that for convenience, members having functions identical to those of the respective members described in Embodiments 1 and 2 are given respective identical reference numerals, and a description of those members is omitted.

The continuous film-feed device 30C of the carbon ion generating device 10E has a configuration identical to the configuration of the continuous film-feed device 30C of the carbon ion generating device 10C. Thus, in the carbon ion generating device 10E, a groove 352C that is provided in a tape head 35C is further widened in a feed direction than the groove 352 of the tape head 35 illustrated in (a) of FIG. 7.

In the carbon ion generating device 10E, the galvanometer mirror 14D constituting a part of a first laser irradiation mechanism is provided in place of the mirror 14 of the carbon ion generating device 10 illustrated in FIG. 1. The galvanometer mirror 14D is an example of a scanning mirror and is also referred to as a galvanometer scanner. The galvanometer mirror 14D a reflecting surface of which minutely vibrates about a rotation axis periodically scans, in the feed direction (a direction of an arrow A illustrated in FIG. 11) in which the film 21C is fed, the laser beam L1 that is incident on the reflecting surface. In Embodiment 6, an irradiation region that is irradiated with the laser beam L1 which is scanned by the galvanometer mirror 14D is set so as to be similar to the beam spot P1D illustrated in (b) of FIG. 10.

In a case where the laser beam L1 which is scanned by the galvanometer mirror 14D is scanned in a direction identical to the feed direction in which the film 21C is fed, the laser beam L1 is preferably synchronized with a feed speed at which the film 21C is fed. A control section C illustrated in FIG. 11 controls a vibration frequency and a rotation angle of the reflecting surface of the galvanometer mirror 14D so that the laser beam L1 which is scanned in the direction identical to the feed direction in which the film 21C is fed is synchronized with the feed speed at which the film 21C is fed.

According to this configuration, in a case where the laser beam L1 is scanned in the direction identical to the feed direction in which the film 21C is fed, the laser beam L1 and the film 21C move in synchronization. Thus, as compared with a case where a single laser beam L1 is not scanned (for example, the case of the carbon ion generating device 10A illustrated in FIG. 7), the configuration makes it possible to irradiate a carbonized region 22C with the laser beam L1 for a longer time without stopping feed of the film 21C. Thus, without stopping feed of the film 21C, it is possible to secure a sufficient time for carbonizing a polyimide resin contained in a region of the film 21C which region is irradiated with the laser beam L1.

In the carbon ion generating device 10E, a power density in an irradiation region that the laser beam L1 forms in the film 21C is preferably determined so as to continuously increase from upstream to downstream in the feed direction in which the film 21C is fed. In Embodiment 6, the control section C controls a laser beam source 12 such that (1) power of the laser beam L1 is set so that a temperature in the irradiation region is 600° C. in a case where the irradiation region is located most upstream, (2) the power of the laser beam L1 is set so that the temperature in the irradiation region is 1000° C. in a case where the irradiation region is located most downstream, and (3) the power of the laser beam L1 is continuously increased from upstream to downstream.

However, in the carbon ion generating device 10E, the power density in the irradiation region that the laser beam L1 forms in the film 21C can be alternatively determined so as to gradually increase from upstream to downstream in the feed direction in which the film 21C is fed. The number of steps in which the power density is increased is not limited and can be determined as appropriate. For example, the power density may be increased in two steps, three steps, or eight steps.

In Embodiment 6, a beam spot that is an irradiation region of the film 21C which irradiation region is irradiated with a laser beam L2 is provided at a position identical to a position at which the beam spot P2 illustrated in (b) of FIG. 10 is provided. The control section C controls a laser beam source 15 such that the film 21C is irradiated with the laser beam L2 when the laser beam L1 which is scanned in synchronization with the feed speed at which the film 21C is fed reaches the negative y-axis direction side end of a scanning range. Thus, the irradiation region that is irradiated with the laser beam L2 is included in the irradiation region that is irradiated with the laser beam L1 when the film 21C is irradiated with the laser beam L2 (see the laser beam L1 that is located on the most negative y-axis direction side among three laser beams L1 illustrated in FIG. 11). This configuration enables the irradiation region that is irradiated with the laser beam L1 to be irradiated with the laser beam L2 during a period in which the carbonized region 22C is irradiated with the laser beam L1. Note, however, that the irradiation region which is irradiated with the laser beam L2 may be set so as to be located further downstream of a range in which the irradiation region that is irradiated with the laser beam L1 which is being scanned is movable. In this case, a shortest distance between the irradiation region that is irradiated with the laser beam L1 and the irradiation region that is irradiated with the laser beam L2 is preferably as short as possible in order to prevent or reduce adhesion of an impurity gas to the carbonized region 22C that has been irradiated with the laser beam L1.

Aspects of the present invention can also be expressed as follows:

A carbon ion generating device in accordance with Aspect 1 of the present invention includes: a first laser irradiation mechanism that generates a carbonized region by irradiating a part of a film made of an organic compound with a first laser beam so as to carbonize the part; and a second laser irradiation mechanism that generates carbon ions from the carbonized region by irradiating at least a part of the carbonized region with a second laser beam.

According to the above configuration, during generation of a carbonized region by irradiating a part of a film with a first laser beam, impurity layers formed on a front surface and a back surface in or near the carbonized region are removed. Thus, Aspect 1 makes it possible to prevent or reduce generation of impurity ions in a carbon ion generating device in which a laser-driven ion acceleration system is employed.

A carbon ion generating device in accordance with Aspect 2 of the present invention employs, in addition to the configuration of the carbon ion generating device in accordance with Aspect 1 described earlier, a configuration such that a wavelength and an output of the first laser beam, and an area of a region of the film which region is irradiated with the first laser beam are determined so that the film in the region is heated to a temperature of not lower than 600° C.

According to the above configuration, while generating a carbonized region in a part of a film by irradiation with a first laser beam, it is possible to remove impurity layers formed on a front surface and a back surface in or near the carbonized region. Thus, Aspect 2 makes it possible to prevent or reduce generation of impurity ions without fail and enhance purity of carbon ions to be generated.

A carbon ion generating device in accordance with Aspect 3 of the present invention employs, in addition to the configuration of the carbon ion generating device in accordance with Aspect 1 or 2 described earlier, a configuration to further include: a holding section that holds the film so that at least a region which is irradiated with the first laser beam and a region which is irradiated with the second laser beam are planar; and a movement section that moves the film, the film being larger than the region which is irradiated with the first laser beam and the region which is irradiated with the second laser beam.

According to the above configuration, by relatively moving respective positions of a region of a film which region is irradiated with the first laser beam and a region of the film which region is irradiated with the second laser beam, it is possible to continuously generate carbon ions a plurality of times while using a single film. Thus, Aspect 3 makes it possible to extend a cycle of replacement of films.

A carbon ion generating device in accordance with Aspect 4 of the present invention employs, in addition to the configuration of the carbon ion generating device in accordance with Aspect 3 described earlier, a configuration such that the film is formed in a form of a tape, the movement section includes a first pulley through which the film is fed and a second pulley around which the film is wound, and the holding section includes a tape head which is provided between the first pulley and the second pulley and which determines a position in a direction normal to a main surface of the film.

According to the above configuration, a movement section can move a position of a film in a predetermined direction. Thus, according to Aspect 4, by moving the film, it is possible to continuously generate carbon ions a plurality of times without moving a region that is irradiated with a first laser beam and a region that is irradiated with a second laser beam.

A carbon ion generating device in accordance with Aspect 5 of the present invention employs, in addition to the configuration of the carbon ion generating device in accordance with Aspect 4 described earlier, a configuration such that the first laser irradiation mechanism further includes a plurality of laser beam sources that emit a respective plurality of sub laser beams constituting the first laser beam, and irradiation regions of the film which irradiation regions are irradiated with the respective plurality of sub laser beams are provided in a feed direction in which the film is fed.

According to the above configuration, irradiation regions can be provided in a plurality of parts of a film to be fed. This makes it possible to irradiate a carbonized region with a first laser beam for a longer cumulative time without stopping feed of a tape. Thus, since it is possible to remove an impurity gas adhering to a surface of the carbonized region, it is possible to prevent or reduce generation of impurity ions without fail and enhance purity of carbon ions to be generated.

A carbon ion generating device in accordance with Aspect 6 of the present invention employs, in addition to the configuration of the carbon ion generating device in accordance with Aspect 5 described earlier, a configuration such that power densities of the sub laser beams in the respective irradiation regions are determined so as to increase from upstream to downstream in the feed direction.

A further increase in power density of a first laser beam achieves an increase in temperature of a carbonized region. This makes it possible to further remove an impurity gas adhering to a surface of the carbonized region. However, in a case where a film is suddenly irradiated with the first laser beam that has a power density high enough to sufficiently remove the impurity gas, the carbonized region may be damaged due to an abrupt change from an organic compound to carbon. According to the above configuration, after setting a plurality of irradiation regions, it is possible to gradually increase power densities of sub laser beams in the respective irradiation regions. Thus, while making it less likely that the carbonized region will be damaged, it is possible to increase purity of carbon ions to be generated.

A carbon ion generating device in accordance with Aspect 7 of the present invention employs, in addition to the configuration of the carbon ion generating device in accordance with Aspect 4 described earlier, a configuration such that in an irradiation region of the film which irradiation region is irradiated with the first laser beam, a length in a feed direction in which the film is fed is longer than a length in a direction orthogonal to the feed direction.

According to the above configuration, it is possible to irradiate a carbonized region with a first laser beam for a longer cumulative time without stopping feed of a tape. Thus, since it is possible to remove an impurity gas adhering to a surface of the carbonized region, it is possible to prevent or reduce generation of impurity ions without fail and enhance purity of carbon ions to be generated.

A carbon ion generating device in accordance with Aspect 8 of the present invention employs, in addition to the configuration of the carbon ion generating device in accordance with Aspect 4 described earlier, a configuration such that the first laser irradiation mechanism further includes a scanning mirror that scans the first laser beam in a feed direction in which the film is fed and in synchronization with a feed speed at which the film is fed.

According to the above configuration, it is possible to irradiate a carbonized region with a first laser beam for a longer cumulative time without stopping feed of a tape. Thus, since it is possible to remove an impurity gas adhering to a surface of the carbonized region, it is possible to prevent or reduce generation of impurity ions without fail and enhance purity of carbon ions to be generated.

A carbon ion generating device in accordance with Aspect 9 of the present invention employs, in addition to the configuration of the carbon ion generating device in accordance with Aspect 8 described earlier, a configuration such that a power density in an irradiation region that the first laser beam forms in the film is determined so as to gradually or continuously increase from upstream to downstream in the feed direction.

According to the above configuration, a first laser beam can be scanned in synchronization with a feed direction in which a film is fed and a feed speed at which the film is fed, and a power density of the first laser beam can be gradually or continuously increased. Thus, while making it less likely that a carbonized region will be damaged, it is possible to increase purity of carbon ions to be generated.

A carbon ion generating device in accordance with Aspect 10 of the present invention employs, in addition to the configuration of the carbon ion generating device in accordance with Aspect 3 described earlier, a configuration such that the film is formed in a circular or polygonal shape, the holding section holds a plurality of parts of an outer edge of the film, and the movement section moves the holding section in an in-plane direction of a main surface of the film.

According to the above configuration, a movement section can move a position of a film in an in-plane direction of the film. Thus, according to Aspect 10, by moving the film, it is possible to continuously generate carbon ions a plurality of times without moving a region that is irradiated with a first laser beam and a region that is irradiated with a second laser beam.

A carbon ion generating device in accordance with Aspect 11 of the present invention employs, in addition to the configuration of the carbon ion generating device in accordance with any one of Aspects 1 through 10 described earlier, a configuration such that the second laser irradiation mechanism carries out irradiation with the second laser beam during a period in which the first laser irradiation mechanism carries out irradiation with the first laser beam.

According to the above configuration, it is possible to prevent an impurity layer from being formed again on a front surface and a back surface in or near a carbonized region after irradiation with a first laser beam. Thus, Aspect 11 makes it possible to further prevent or reduce generation of impurity ions and further enhance purity of carbon ions to be generated.

A carbon ion generating device in accordance with Aspect 12 of the present invention employs, in addition to the configuration of the carbon ion generating device in accordance with any one of Aspects 3 through 10 described earlier, a configuration such that a region which is irradiated with the first laser beam and a region which is irradiated with the second laser beam are different in position in the film, and the movement section moves the film so that the carbonized region which has been generated by being irradiated with the first laser beam overlaps the region which is irradiated with the second laser beam.

According to the above configuration, carbon ions are generated by sequentially moving, to the region which is irradiated with the second laser beam, carbonized regions that have been generated in the region which is irradiated with the first laser beam. Thus, since it is possible to concurrently carry out generation of the carbonized regions and generation of carbon ions from the carbonized regions, Aspect 12 achieves an increase in repetition frequency at which the carbon ions are generated.

A carbon ion generating device in accordance with Aspect 13 of the present invention employs, in addition to the configuration of the carbon ion generating device in accordance with any one of Aspects 1 through 12 described earlier, a configuration such that the film has a thickness that is not more than 12.5 μm.

In a case where one (e.g., referred to as a front surface) of surfaces of a film is irradiated with a second laser beam, electrons in the film which have been excited by the second laser beam travel toward the other (e.g., referred to as a back surface) of the surfaces of the film while diffusing through the film. Thus, a greater thickness of the film results in an increase in region of the back surface of the film in which region a sheath electric field is formed (i.e., region in which carbon ions are generated). An increase in region in which a sheath electric field is formed means that the sheath electric field has a lower intensity due to a lower electron density in the region. The intensity of the sheath electric field and acceleration energy of carbon ions to be generated are positively correlated with each other. Thus, the sheath electric field preferably has a higher intensity in order to generate acceleration energy of carbon ions having high acceleration energy. According to the above configuration, it is possible to generate carbon ions acceleration energy of which has a maximum value that reaches 8.5 MeV.

Furthermore, a region in which carbon ions are generated is preferably small so that the generated carbon ions are controlled downstream of the region. According to the above configuration, it is possible to prevent a region in which carbon ions are generated from being too large. This makes it easy to control the carbon ions downstream of the region.

A carbon ion generating device in accordance with Aspect 14 of the present invention employs, in addition to the configuration of the carbon ion generating device in accordance with any one of Aspects 1 through 13 described earlier, a configuration such that the film is made of a polyimide resin.

A polyimide resin film is easily available and has a sufficiently high mechanical strength. Thus, a polyimide resin is suitable as a material of which a film is made. Furthermore, polyimide resin films that have various thicknesses are on the market, and, for example, a polyimide resin film having a thickness as thin as approximately 5 μm can be stably obtained. Also in this respect, a polyimide resin is suitable as a material of which a film is made.

ADDITIONAL REMARKS

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

10, 10A, 10B Carbon ion generating device
12 Laser beam source (first laser beam source)
L1 Laser beam (first laser beam)
15 Laser beam source (second laser beam source)
L2 Laser beam (second laser beam)
21, 21A, 21B Film
22, 22A, 22B Carbonized region
P1 Beam spot (region irradiated with first laser beam)
P2 Beam spot (region irradiated with second laser beam)
P3 Ion generation region
30, 40 Continuous film-feed device
311, 312 Pulley (first pulley, second pulley, part of movement section)
35 Tape head
351 Head surface
361, 362 Motor (part of movement section)
41 Rotational movement stage
411 Stage (part of movement section)
4111 Stage body
4112 Back plate
412 Cross-roller ring (part of movement section)
413 Fastener
414 Base material
4141 Base material body
4142 Back plate
415 Motor (part of movement section)
416 Pulley (part of movement section)
417 Belt (part of movement section)
42 Horizontal movement stage (part of movement section)
421 Base material
422 Stage

The invention claimed is:

1. A carbon ion generating device comprising:

a first laser irradiation mechanism that generates a carbonized region by irradiating a part of a film made of an organic compound with a first laser beam so as to carbonize the part; and a second laser irradiation mechanism that generates carbon ions from the carbonized region by irradiating at least a part of the carbonized region with a second laser beam.

2. The carbon ion generating device as set forth in claim 1, wherein a wavelength and an output of the first laser beam, and an area of a region of the film which region is irradiated with the first laser beam are determined so that the film in the region is heated to a temperature of not lower than 600° C.

3. A carbon ion generating device as set forth in claim 1, further comprising:

a holding section that holds the film so that at least a region which is irradiated with the first laser beam and a region which is irradiated with the second laser beam are planar; and a movement section that moves the film, the film being larger than the region which is irradiated with the first laser beam and the region which is irradiated with the second laser beam.

4. The carbon ion generating device as set forth in claim 3, wherein the film is formed in a form of a tape, the movement section includes a first pulley through which the film is fed and a second pulley around which the film is wound, and the holding section includes a tape head which is provided between the first pulley and the second pulley and which determines a position in a direction normal to a main surface of the film.

5. The carbon ion generating device as set forth in claim 4, wherein the first laser irradiation mechanism further includes a plurality of laser beam sources that emit a respective plurality of sub laser beams constituting the first laser beam, and irradiation regions of the film which irradiation regions are irradiated with the respective plurality of sub laser beams are provided in a feed direction in which the film is fed.

6. The carbon ion generating device as set forth in claim 5, wherein power densities of the sub laser beams in the respective irradiation regions are determined so as to increase from upstream to downstream in the feed direction.

7. The carbon ion generating device as set forth in claim 4, wherein in an irradiation region of the film which irradiation region is irradiated with the first laser beam, a length in a feed direction in which the film is fed is longer than a length in a direction orthogonal to the feed direction.

8. The carbon ion generating device as set forth in claim 4, wherein the first laser irradiation mechanism further includes a scanning mirror that scans the first laser beam in a feed direction in which the film is fed and in synchronization with a feed speed at which the film is fed.

9. The carbon ion generating device as set forth in claim 8, wherein a power density in an irradiation region that the first laser beam forms in the film is determined so as to gradually or continuously increase from upstream to downstream in the feed direction.

10. The carbon ion generating device as set forth in claim 3, wherein the film is formed in a circular or polygonal shape, the holding section holds a plurality of parts of an outer edge of the film, and the movement section moves the holding section in an in-plane direction of a main surface of the film.

11. The carbon ion generating device as set forth in claim 1, wherein the second laser irradiation mechanism carries out irradiation with the second laser beam during a period in which the first laser irradiation mechanism carries out irradiation with the first laser beam.

12. The carbon ion generating device as set forth in claim 3, wherein a region which is irradiated with the first laser beam and a region which is irradiated with the second laser beam are different in position in the film, and the movement section moves the film so that the carbonized region which has been generated by being irradiated with the first laser beam overlaps the region which is irradiated with the second laser beam.

13. The carbon ion generating device as set forth in claim 1, wherein the film has a thickness that is not more than 12.5 um.

14. The carbon ion generating device as set forth in claim 1, wherein the film is made of a polyimide resin.

* * * * *